(12) United States Patent
Araki et al.

(10) Patent No.: US 8,178,322 B2
(45) Date of Patent: May 15, 2012

(54) METHOD FOR PRODUCING AN L-AMINO ACID OR A NUCLEIC ACID

(75) Inventors: Masayuki Araki, Kawasaki (JP);
Yusuke Takahashi, Kawasaki (JP);
Akihiro Watanabe, Kawasaki (JP);
Fumito Ohnishi, Kawasaki (JP);
Takahiro Asano, Kawasaki (JP);
Kazuya Kondo, Kawasaki (JP); Wataru Hibino, Kawasaki (JP); Shintaro Iwatani, Kawasaki (JP); Satoshi Okutani, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 308 days.

(21) Appl. No.: 12/541,204

(22) Filed: Aug. 14, 2009

(65) Prior Publication Data
US 2010/0062493 A1    Mar. 11, 2010

Related U.S. Application Data

(63) Continuation of application No. PCT/JP2008/050135, filed on Jan. 9, 2008.

(30) Foreign Application Priority Data

Feb. 20, 2007    (JP) ................. 2007-039843

(51) Int. Cl.
| | |
|---|---|
| *C12P 19/40* | (2006.01) |
| *C12P 19/30* | (2006.01) |
| *C12P 19/34* | (2006.01) |
| *C12P 13/04* | (2006.01) |
| *C12P 13/22* | (2006.01) |
| *C12P 13/12* | (2006.01) |
| *C12P 13/08* | (2006.01) |
| *C12P 13/06* | (2006.01) |

(52) U.S. Cl. ............. 435/88; 435/89; 435/90; 435/91.1; 435/106; 435/108; 435/110; 435/113; 435/115; 435/116

(58) Field of Classification Search .............. 435/91.1, 435/106, 108, 110, 113, 115, 116, 88, 89, 435/90
See application file for complete search history.

(56) References Cited

U.S. PATENT DOCUMENTS

| | | | |
|---|---|---|---|
| 4,371,614 A | 2/1983 | Anderson et al. |
| 4,987,072 A | 1/1991 | Reichenbach et al. |
| 5,001,059 A | 3/1991 | Skatrud et al. |
| 5,518,904 A | 5/1996 | Igarashi et al. |
| 5,547,858 A | 8/1996 | Nagano et al. |
| 6,180,373 B1 | 1/2001 | Wich et al. |
| 6,905,819 B1 | 6/2005 | Matsuzaki et al. |
| 6,960,455 B2 | 11/2005 | Livshits et al. |
| 7,015,010 B1 | 3/2006 | Izui et al. |
| 7,045,320 B2 | 5/2006 | Iwatani et al. |
| 7,306,933 B2 | 12/2007 | Van Dien et al. |
| 7,354,744 B2 | 4/2008 | Takahashi et al. |
| 2009/0142814 A1 | 6/2009 | Murakoshi et al. |
| 2009/0148915 A1 | 6/2009 | Van Dien et al. |

FOREIGN PATENT DOCUMENTS

| | | |
|---|---|---|
| EP | 1 870 476 | 12/2007 |
| JP | 62-000288 | 1/1987 |
| JP | 62-030735 | 2/1987 |
| JP | 62-244382 | 10/1987 |
| JP | 63-214189 | 9/1988 |

OTHER PUBLICATIONS

International Preliminary Report on Patentability for PCT Patent App. No. PCT/JP2008/050135 (Sep. 3, 2009).
International Search Report for PCT/JP2008/050135 (Apr. 8, 2008).
U.S. Appl. No. 12/033,374, filed Feb. 19, 2008, Takahashi et al.
U.S. Appl. No. 12/055,438, filed Mar. 26, 2008, Iwatani et al.
U.S. Appl. No. 61/154,500, filed Feb. 23, 2009, Iwatani et al.
U.S. Appl. No. 12/419,409, filed Apr. 7, 2009, Okutani et al.
U.S. Appl. No. 12/420,934, filed Apr. 9, 2009, Tajima et al.

*Primary Examiner* — Herbert J Lilling
(74) *Attorney, Agent, or Firm* — Shelly Guest Cermak; Cermak Nakajima LLP

(57) ABSTRACT

A method is described for producing an L-amino acid or a nucleic acid by culturing a microorganism having an ability to produce the L-amino acid or nucleic acid in a liquid medium in a fermentation tank containing a stirring impeller, and optionally adding seed crystals to the medium as required to produce and accumulate crystals of the L-amino acid or nucleic acid in the medium, and collecting crystals of the L-amino acid or nucleic acid from the culture. The power density of the stirring impeller is controlled to be 2.4 kW/m$^3$ or lower after either precipitation of the crystals or addition of the seed crystals.

9 Claims, 3 Drawing Sheets

SEQUENCE LISTING

```
<160> NUMBER OF SEQ ID NOS: 4

<210> SEQ ID NO 1
<211> LENGTH: 33
<212> TYPE: DNA
<213> ORGANISM: Artificial
<220> FEATURE:
<223> OTHER INFORMATION: primer 1

<400> SEQUENCE: 1
ggaagatcta tttgccttcg cacatcaacc tgg                            33

<210> SEQ ID NO 2
<211> LENGTH: 30
<212> TYPE: DNA
<213> ORGANISM: Artificial
<220> FEATURE:
<223> OTHER INFORMATION: primer 2

<400> SEQUENCE: 2
cggggtacct tgtaaatatt ttaacccgcc                               30

<210> SEQ ID NO 3
<211> LENGTH: 56
<212> TYPE: DNA
<213> ORGANISM: Artificial
<220> FEATURE:
<223> OTHER INFORMATION: primer 3

<400> SEQUENCE: 3
ggaagatcta aggagacctt aaatgagcga cacaacgatc ctgcaaaaca gtaccc   56

<210> SEQ ID NO 4
<211> LENGTH: 39
<212> TYPE: DNA
```

```
<213> ORGANISM: Artificial
<220> FEATURE:
<223> OTHER INFORMATION: primer 4

<400> SEQUENCE: 4
cggggtacct cgtagaggtt tactggcgct tatccagcg                        39
```

METHOD FOR PRODUCING AN L-AMINO ACID OR A NUCLEIC ACID

This application is a continuation under 35 U.S.C. §120 of PCT Patent Application No. PCT/JP2008/050135, filed Jan. 9, 2008, which claims priority under 35 U.S.C. §119 to Japanese Patent Application No. 2007-039843, filed on Feb. 20, 2007, which are incorporated in their entireties by reference. The Sequence Listing in electronic format filed herewith is also hereby incorporated by reference in its entirety (File Name: US-400_Seq_List; File Size: 1 KB; Date Created: Aug. 14, 2009).

BACKGROUND OF THE INVENTION

1. Field of the Invention

The present invention relates to techniques used in the fermentation industry, more specifically, a method for producing an L-amino acid or nucleic acid by fermentation using a microorganism, in which culture is performed with precipitating the L-amino acid or nucleic acid.

2. Brief Description of the Related Art

L-Amino acids are industrially produced by fermentation using L-amino acid-producing bacteria belonging to the coryneform bacteria or the family Enterobacteriaceae. As these amino acid-producing bacteria, strains isolated from the nature as well as artificial mutants of such strains and recombinant strains in which L-amino acid biosynthesis enzyme is enhanced by genetic recombination are used in order to improve the productivity.

Examples of such bacteria include, for example, for L-tryptophan fermentation, a bacterium with enhanced anthranilate synthetase activity, phosphoglycerate dehydrogenase activity, and tryptophan synthase activity (WO94/08031), and bacteria in which the tryptophan operon is amplified (Japanese Patent Laid-open (Kokai) Nos. 57-71397 and 62-244382, U.S. Pat. No. 4,371,614).

Examples of the techniques for L-glutamic acid fermentation include increasing L-glutamic acid-producing ability by enhancing the glutamate dehydrogenase gene (gdh), isocitrate dehydrogenase gene (icdA), aconitate hydratase gene (acnA, acnB), and citrate synthase gene (gltA) (Japanese Patent Laid-open No. 63-214189).

Examples of bacteria for L-threonine fermentation include microorganisms in which one or more of the following genes are enhanced: the gene encoding aspartokinase III (lysC), aspartate semialdehyde dehydrogenase (asd), aspartokinase I (thrA), homoserine kinase (thrB), and threonine synthase (thrC), and so forth. The thrA, thrB, and thrC are all encoded by the thr operon (Japanese Patent Laid-open No. 2001-346578).

Although L-amino acid-producing abilities are considerably increased by the aforementioned breeding of microorganisms and improvement of production methods, it is still desirable for more inexpensive and efficient methods for producing L-amino acids to be developed in order to respond to increase in demand in the future.

Methods of performing fermentation while L-amino acids are precipitating in a culture medium are also known (Japanese Patent Laid-open No. 62-288, European Patent No. 1078989). As for L-glutamic acid, a method for producing L-glutamic acid by using a microorganism which can accumulate L-glutamic acid with its precipitation has been disclosed (U.S. Pat. No. 6,905,819). Moreover, a fermentation method utilizing crystallization in which crystals of amino acid having a mean particle diameter of 1 to 120 μm are added to medium is also known (WO06/109830).

However, productivities of the aforementioned methods are insufficient as compared to those obtainable in usual fermentation methods in which crystals are not precipitated, and further improvements have been desired.

SUMMARY OF THE INVENTION

An aspect of the present invention is to improve productivity during the production of L-amino acids or nucleic acids by fermentation using a microorganism in which the L-amino acid or nucleic acid precipitates in a medium in the form of crystals.

It is generally assumed that reducing the power density of stirring impeller used in fermentation adversely affects the fermentation. However, it was found that the productivity of L-amino acids can be improved by controlling the power density of the stirring impeller so that it is lower than a certain level after the precipitation of the crystals or the addition of seed crystals.

It is an aspect of the present invention to provide a method for producing an L-amino acid or a nucleic acid comprising culturing a microorganism having an ability to produce the L-amino acid or nucleic acid in a liquid medium in a fermentation tank containing a stirring impeller, and optionally adding seed crystals to the medium as required, and allowing crystals of the L-amino acid or nucleic acid to accumulate in the medium, and collecting crystals of the L-amino acid or nucleic acid from the medium, wherein the power density of the stirring impeller is controlled to be 2.4 kW/m$^3$ or lower after either precipitation of the crystals or the addition of seed crystals.

It is a further aspect of the present invention to provide the aforementioned method, wherein the power density of the stirring impeller is controlled to be 0.5 kW/m$^3$ or higher after either precipitation of the crystals or addition of the seed crystals.

It is a further aspect of the present invention to provide the aforementioned method, wherein the power density of the stirring impeller is controlled to be 3.0 kW/m$^3$ or higher before either precipitation of the crystals or addition of the seed crystals.

It is a further aspect of the present invention to provide the aforementioned method, wherein the microorganism belongs to the family Enterobacteriaceae.

It is a further aspect of the present invention to provide the aforementioned method, wherein the microorganism is a coryneform bacterium or a *Bacillus* bacterium.

It is a further aspect of the present invention to provide the aforementioned method, wherein the L-amino acid is selected from the group consisting of L-tryptophan, L-phenylalanine, L-tyrosine, L-isoleucine, L-valine, L-leucine, L-glutamic acid, L-glutamine, L-threonine, L-cysteine, L-cystine, derivatives thereof, and combinations thereof.

It is a further aspect of the present invention to provide the aforementioned method, wherein the nucleic acid is selected from the group consisting of inosine, adenosine, guanosine, xanthosine, inosinic acid, adenylic acid, guanylic acid, xanthylic acid, derivatives thereof, and combinations thereof.

DETAILED DESCRIPTION OF THE PREFERRED EMBODIMENTS

<1> Production Method

Figure 1:
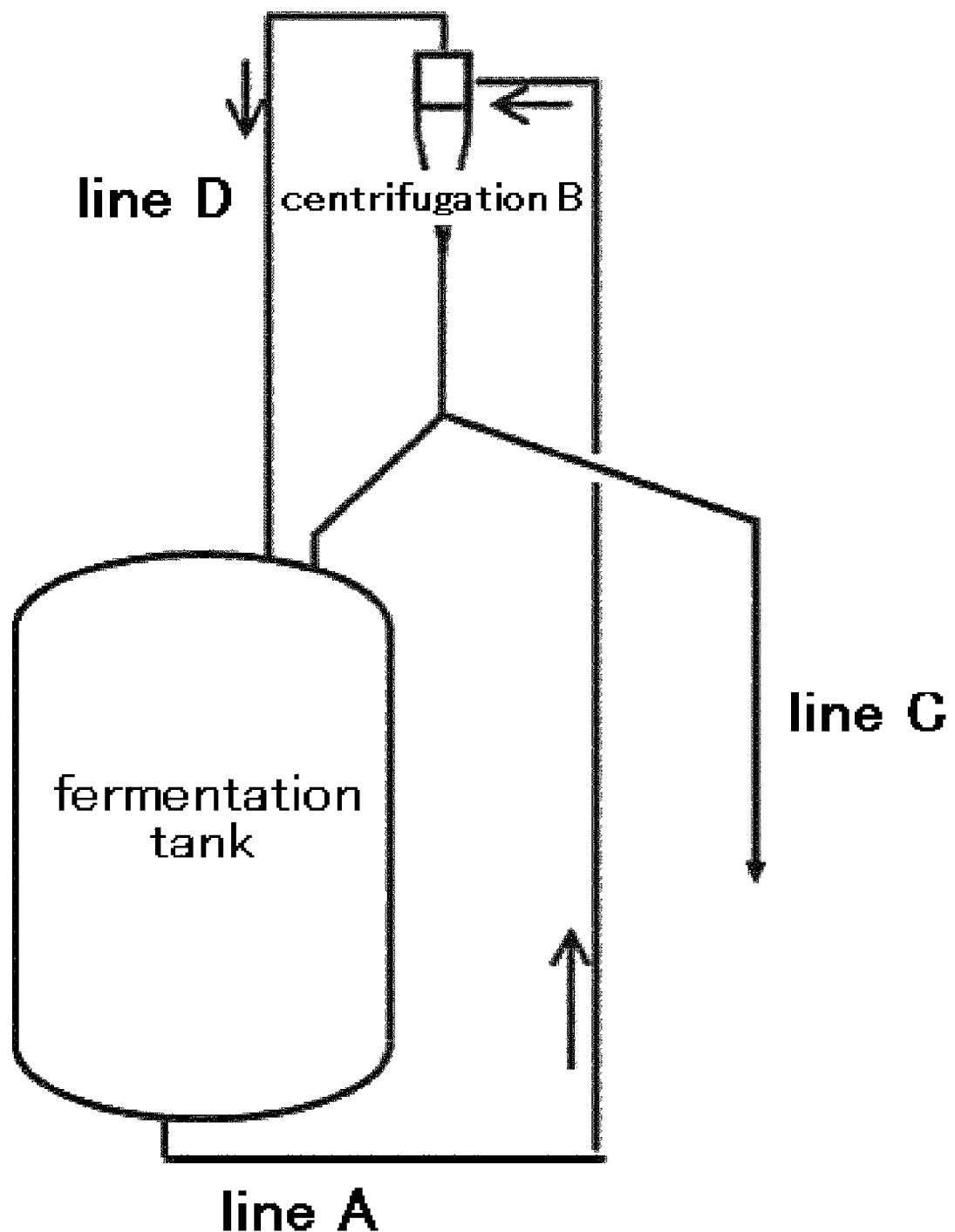
FIG. 1 shows a schematic view of a fermentation apparatus, which shows collection of a target substance from a fermentation tank.

An exemplary method of the present invention is to produce an L-amino acid or a nucleic acid by culturing a microorganism having an ability to produce the L-amino acid or nucleic acid in a liquid medium in a fermentation tank containing a stirring impeller, and optionally adding seed crystals to the medium as required, to produce and accumulate crystals of the L-amino acid or nucleic acid in the medium, and collecting crystals of the L-amino acid or nucleic acid from culture, wherein the power density of the stirring impeller (power per unit volume of the fermentation broth) is controlled to be 2.4 kW/m$^3$ or lower after either precipitation of the crystals or addition of the seed crystals.

The "L-amino acid" is not particularly limited so long as the amino acid can be produced in a medium by precipitation during fermentation using microorganisms. Examples include basic amino acids such as L-lysine, L-ornithine, L-arginine, L-histidine, and L-citrulline; aliphatic L-amino acids such as L-isoleucine, L-alanine, L-valine, L-leucine, and L-glycine; L-amino acids which are hydroxymonoaminocarboxylic acids such as L-threonine and L-serine; cyclic L-amino acids such as L-proline; aromatic L-amino acids such as L-phenylalanine, L-tyrosine, and L-tryptophan; sulfur-containing L-amino acids such as L-cysteine, L-cystine, and L-methionine; acidic L-amino acids such as L-glutamic acid, and L-aspartic acid; L-amino acids with amide group at the side chain such as L-glutamine, and L-asparagine, etc.

Hydrophobic amino acids, acidic amino acids, and amino acids with an amide group at the side chain are exemplified. Exemplary hydrophobic amino acids include L-valine, L-leucine and L-isoleucine, which are aliphatic amino acids, and L-tryptophan, L-phenylalanine and L-tyrosine, which are aromatic amino acids. Exemplary acidic amino acids include L-glutamic acid and L-aspartic acid. Exemplary amino acids with an amide group at the side chain include L-glutamine, L-asparagine, and so forth.

Moreover, the term "L-amino acid" can also include derivatives of and obtained from the aforementioned amino acids, and examples include GABA, p-hydroxy-D-phenylglycine, DOPA, succinic acid, malic acid, and pyruvic acid.

The L-amino acid or nucleic acid can include one or two or more kinds of L-amino acids or nucleic acids.

The "nucleic acid" is not particularly limited, so long as it is a nucleic acid that can be produced by precipitation in a medium during fermentation utilizing a microorganism. Examples of the nucleic acid include purine nucleosides, purine nucleotides, and so forth. Exemplary purine nucleosides include inosine, xanthosine, guanosine, adenosine, and so forth, and exemplary purine nucleotides include 5'-phosphate esters of the purine nucleosides, for example, inosinic acid, (inosine-5'-phosphate, henceforth also referred to as "IMP"), xanthylic acid (xanthosine-5'-phosphate, henceforth also referred to as "XMP"), guanylic acid (guanosine-5'-monophosphate, henceforth also referred to as "GMP"), adenylic acid (adenosine-5'-monophosphate, henceforth also referred to as "AMP"), and so forth. The nucleic acid includes nucleic acid derivatives of and obtained from the aforementioned nucleic acids, and examples include Ara-U (uracil arabinoside), ZVA (Z-valacyclovir), and so forth. The aforementioned L-amino acids, nucleic acids and derivatives thereof can also be referred to as the "target substance".

The stirring impeller is a device for stirring a liquid medium in a fermentation tank, and the shape of the impeller is not particularly limited. The stirring impeller can include an axis and fins (blades) fixed on the axis, or the fins or a part thereof can constitute the axis. The stirring impeller usually rotates around the axis as the center, but it can operate in other ways. The shape of the fins can include, but is not limited to, and form such as a turbine, paddle, propeller, anchor, ribbon, or the like. Moreover, the number of fins and the disposition of each fin are also not particularly limited. The stirring impeller operates upon receiving power with the axis from a power source such as a motor. Information about the stirring impeller can be obtained from, for example, Chemical Engineering Manual (Kagaku Kogaku Binran, edited by Chemical Engineering Association, revised 4th edition, pp. 1310-1311, Maruzen Co., Ltd.

The "power density" of the stirring impeller means the power of the stirring impeller per unit volume of fermentation broth. Power of the stirring impeller is calculated by subtracting power (output) provided by a power source while stirring in an empty fermentation tank from power (output) provided by a power source while stirring the fermentation broth. Specifically, the power can be calculated from, for example, when the power source is a motor, the current which flows through the motor and the efficiency of the motor. The power can also be measured by preparing a calibration curve showing the relation of the current which flows through the motor and the power, and converting the current into power using the calibration curve. Furthermore, the power can also be calculated in accordance with the following equation from a value of torque applied on the stirring impeller, which is measured by using an instrument for measuring torque, such as a torque meter or torque sensor.

$$\text{Power } P[\text{kW}] = T \times 2 \times \pi \times n / 1000$$

T: Torque [N·m]

n: Rotation number of stirring impeller [/s]

The value obtained by dividing the power measured as described above by the volume of the medium is the power density of the stirring impeller.

The power density of the stirring impeller can be controlled to be 2.4 kW/m$^3$ or lower after either precipitation of the crystals or addition of seed crystals. The power density of the stirring impeller is controlled to be, for example, 2.0 kW/m$^3$ or lower, 1.5 kW/m$^3$ or lower in another example, 1.0 kW/m$^3$ or lower in another example. Although the lower limit of the power density of the stirring impeller is not particularly defined, so long as the production of the target substance or growth of the microorganism are not reduced, it can be controlled to be, for example, 0.4 kW/m$^3$ or higher, 0.5 kW/m$^3$ or higher in another example, 0.6 kW/m$^3$ or higher in another example, 0.7 kW/m$^3$ or higher in another example.

The power density of the stirring impeller is controlled to be within the aforementioned range after either precipitation of crystals or addition of seed crystals, and it can be continuously controlled as described above until completion of the fermentation. Moreover, if the power density of the stirring impeller is substantially controlled to be within the mentioned range, it can temporarily exceed the aforementioned range. Specifically, if the power density of the stirring impeller is within the aforementioned range for 50% or more, 70% or more in another example, 90% or more in another example, of the time period which occurs after either precipitation of the crystals or addition of seed crystals until fermentation or accumulation of target substance reaches a plateau, the power density of the stirring impeller is substantially controlled.

The power density of the stirring impeller before either precipitation of crystals or addition of seed crystals may be higher than the aforementioned range defined for the time period after either precipitation of crystals or after addition of seed crystals, and it is controlled to be, for example, 2.6 kW/m$^3$ or higher, 2.8 kW/m$^3$ or higher in another example, 3.0 kW/m$^3$ or higher in another example. If the power density of the stirring impeller is substantially controlled to be within the above range, it may be temporarily lower than the aforementioned range. Specifically, if the power density of the stirring impeller is within the aforementioned range for 50% or more, 70% or more in another example, 90% or more in another example, of the time period from the start of the fermentation or the target substance production period described later until precipitation of crystals or addition of seed crystals, the power density of the stirring impeller is substantially controlled.

If the amount of the accumulated target substance exceeds the saturation solubility of the target substance, or exceeds oversaturation, the crystals of the target substance spontaneously precipitate. Therefore, if the microorganism is able to produce the target substance in the medium in an amount which exceeds the saturation solubility, actively inducing precipitation of the target substance is not necessary. However, in order to promote precipitation of the target substance, seed crystals can be added. The seed crystals include crystals which are added to the medium as required to induce precipitation. The seed crystals are not limited to crystals of the target substance, but any crystals can be used so long as the crystals are effective for promoting precipitation of the crystals of the target substance. However, crystals of the same substance as the target substance can be used. For example, in the case of L-tryptophan fermentation, crystals of L-tryptophan are on example.

The concentration of the added seed crystals can be, for example, when the microorganism which produces the target substance is able to precipitate crystals in the medium during the fermentation process, about 0.5 g/L or more, 1 g/L or more in another example, 5 g/L or more in another example, and 10 g/L or more in another example.

When the microorganism is not able to produce the target substance in the medium in an amount which exceeds the saturation solubility, it is necessary to add the target substance to the medium so that concentration of the target substance exceeds the saturation solubility. Although the added target substance can be in the form of a solution, fine particles, or crystals, it can contain crystals which act as seed crystals. In this case, the amount of the seed crystals is, for example, 10 g/L or more, 20 g/L or more in another example, 30 g/L or more in another example, and 50 g/L or more in another example. Any substance that is added in order to promote precipitation of the target substance, whether it is a solution or a powder, is included within the scope of the seed crystal, unless otherwise specified.

In any case, as for the upper limit of the concentration of the added seed crystals, the concentration is not particularly defined, so long as the production of the target substance and the growth of the microorganism is not markedly decreased. However, it can be 100 g/L or lower, 90 g/L or lower in another example, 80 g/L or lower in another example, 70 g/L or lower in another example.

Although the seed crystals can be added any time before the microorganism which is able to produce the target substance is inoculated into the medium, or anytime after the microorganism is inoculated into the medium, the seed crystals can be added, for example, after the microorganism is inoculated to the medium, and around when the concentration of the target substance in the medium reaches the saturation solubility but before crystals of the target substance precipitate in the medium. In another example, the seed crystals can be added when the concentration of the target substance is at supersaturation, but before crystals of the target substance precipitate in the medium. To allow for this to occur, the culture time can be extended around 5 hours, around 10 hours in another example, around 15 hours in another example, around 20 hours in another example, around 25 hours in another example, from the start of the culture, or the start of the target substance production stage described later. If the total culture period or the period from the beginning of the target substance production stage to the completion of the culture is equal to 1, the seed crystals can be added when about 0.2, about 0.3 in another example, about 0.4 in another example, of this time period has passed. The saturation solubility means when the concentration of the target substance in the liquid medium is saturated. That is, it means when a steady concentration of the target substance is obtained and the supersaturation of the target substance no longer exists.

The solubilities of L-amino acids and nucleic acids are as shown in Tables 1 and 2, and the seed crystals can be added around when the concentration reaches any of these concentrations.

TABLE 1

| L-Amino acid | Solubility (20° C.) g/L | Solubility (40° C.) g/L |
|---|---|---|
| L-tryptophan | 10.6 | 14 |
| L-phenylalanine | 27.4 | 38 |
| L-tyrosine | 0.38 | 0.75 |
| L-isoleucine | 41.2 | 44 |
| L-leucine | 23.8 | 26 |
| L-valine | 57.5 | 65 |
| L-glutamic acid | 7.2 | 15 |
| L-threonine | 90 | 122 |
| L-glutamine | 37.3 | 66 |
| L-histidine | 38 | 58 |
| L-aspartic acid | 6.0 | 8.3 |
| L-cysteine | 160 | |
| L-cystine | 0.09 | |

TABLE 2

| Nucleoside or nucleotide | Solubility (20° C.) g/L | Solubility (40° C.) g/L |
|---|---|---|
| inosine | 44.4 | 83.4 |
| guanosine | 0.42 | 1.05 |
| adenosine | 3.0 | 8.3 |
| inosinic acid | 137 | 241 |
| guanylic acid | 206 | 260 |

The time period after precipitation of the crystals means the time after the concentration of the target substance in the medium exceeds the saturation solubility, and crystals of the target substance precipitate. The power of the stirring impeller before either the precipitation of crystals or addition of seed crystals can be higher than that after the precipitation of crystals or addition of seed crystals. Although the power of the stirring impeller before the precipitation of crystals or addition of seed crystals can be any power so long as it is within a range which is effective for the growth of the microorganism, it can be controlled to be, for example, 2.4 kW/m$^3$ or higher, 2.6 kW/m$^3$ or higher in another example, 2.8 kW/m³ or higher in another example, 3.0 kW/m³ or higher in another example, 3.2 kW/m³ or higher in another example.

Exemplary methods of the present invention can include a stage for proliferating a microorganism having an ability to produce a target substance (proliferation phase) and a stage for producing the target substance (target substance production phase). In such a case, the microorganism can be allowed to sufficiently grow in the proliferation stage, and maximally produce the target substance in the target substance production phase. Moreover, precipitation of the target substance or addition of seed crystals can be attained in the final stage of the growth phase or the target substance production phase. The total amount of seed crystals can be added at once, or in two or more divided portions which are added at different times, or they can be added continuously.

The "proliferation phase" means the stage when the carbon source is primarily used for cell growth, that is, the stage when the microorganism is logarithmically proliferating. The "target substance production phase" means the stage when the carbon source is mainly used for target substance production, and typically occurs after a period of 10 hours, 15 hours in another example, 20 hours in another example, from the start of the culture.

The power of the stirring impellers in the proliferation phase is not particularly limited, so long as it is within a range suitable for growth of the microorganism, and specifically, it is the same as the power of the stirring impellers used before either the precipitation of crystals or addition of seed crystals described above.

Any medium can be used so long as it contains a carbon source and a nitrogen source as nutrients. As a culture method, any of batch culture, fed-batch culture, or continuous culture can be used.

The fed-batch culture refers to a culture method in which the medium is continuously or intermittently fed into the culture vessel, and the medium is not extracted until the end of the culture. The continuous culture means a method in which the medium is continuously or intermittently fed into the culture vessel during the culture, and the medium is extracted from the vessel (usually in a volume equivalent to the volume of the fed medium) at the same time. The "starting medium" means the medium used in the batch culture before feeding the feed medium in the fed-batch culture or continuous culture, and the "feed medium" means the medium which is supplied to a fermenter when fed-batch culture or continuous culture is performed. The feed medium can contain all or a part of the components necessary for the growth of a microorganism. The term "fermentation medium" means a medium in a fermenter, and a target substance is collected from this fermentation medium. Furthermore, the term "fermenter" means a vessel in which the target substance production is performed, and the shape of this vessel is not limited. For example, a fermentation tank or a jar fermenter can be used. Furthermore, the volume of the fermenter is not limited so long as a target substance can be produced and collected.

As the carbon source in the medium, saccharides such as glucose, glycerol, fructose, sucrose, maltose, mannose, galactose, starch hydrolysate, and molasses can be used, and glucose and sucrose are particular examples. In addition, organic acids such as acetic acid and citric acid and alcohols such as ethanol and methanol can also be used independently or in combination with another carbon source. Furthermore, as a raw material of the carbon source, cane molasses, beet molasses, high test molasses, citrus molasses and invert sugar can be used, and hydrolysates of natural raw materials such as cellulose, starch, corn, cereal, and tapioca can also be used. Furthermore, carbon dioxide dissolved in the culture medium can also be used as the carbon source. These carbon sources can be used in the starting medium and feed medium. The medium can contain one or two or more kinds of these carbon sources. Furthermore, the same carbon source can be used for the starting medium and the feed medium, or the carbon source of the feed medium can be different from that of the starting medium. For example, glucose can be used as the carbon source of the starting medium, while sucrose can be used as the carbon source of the feed medium.

As the nitrogen source in the medium, ammonia, ammonium salts such as ammonium sulfate, ammonium carbonate, ammonium chloride, ammonium phosphate and ammonium acetate, urea, nitrates, and so forth can be used. Ammonia gas and aqueous ammonia used to adjust the pH can also be utilized as the nitrogen source. Furthermore, peptone, yeast extract, meat extract, malt extract, corn steep liquor, soybean hydrolysate, and so forth can also be utilized. The medium can contain one or more kinds of these nitrogen sources. These nitrogen sources can also be used for both the starting medium and the feed medium. Furthermore, the same nitrogen source can be used for both the starting medium and the feed medium, or the nitrogen source of the feed medium can be different from that of the starting medium.

The medium can contain a phosphoric acid source in addition to the carbon source and the nitrogen source. As the phosphoric acid source, potassium dihydrogenphosphate, dipotassium hydrogenphosphate, phosphate polymers such as pyrophosphoric acid, and so forth can be utilized.

Furthermore, the medium can contain a growth promoting factor (a nutrient with a growth promoting effect), in addition to the carbon source and nitrogen source. As the growth promoting factor, trace metals, amino acids, vitamins, fatty acids, nucleic acids as well as peptone, casamino acid, yeast extract, soybean protein degradation product, and so forth containing the foregoing substances can be used. Aromatic amino acids and branched chain amino acids, in particular, share a common biosynthesis system, and therefore a biosynthesis system of the microorganism for an amino acid other than the target amino acid can be attenuated as described later. In such a case, the amino acid for which the biosynthesis system is attenuated can be added to the medium. For example, when the target amino acid is L-tryptophan, L-phenylalanine and/or tyrosine can be added, and when the target amino acid is L-phenylalanine, it is desirable to add L-tryptophan and/or L-tyrosine (WO2003/048374).

Examples of the trace metals include iron, manganese, magnesium, calcium, and so forth. Examples of the vitamins include vitamin $B_1$, vitamin $B_2$, vitamin $B_6$, nicotinic acid, nicotinic acid amide, vitamin $B_{12}$, pyridoxine, pantothenic acid, and so forth. These growth promoting factors can be present in the starting medium or the feed medium.

Furthermore, when an auxotrophic mutant that requires an amino acid or the like for growth is used, the required nutrient can be supplemented to the medium. In particular, since an L-amino acid biosynthetic pathway is enhanced and an L-amino acid degrading ability is often attenuated in an L-amino acid-producing bacteria as described later, one or more of L-lysine, L-homoserine, L-isoleucine, and L-methionine can be added. For nucleic acid-producing bacteria, required substances can be similarly added to the medium.

The starting medium and the feed medium can have the same or different compositions. Furthermore, when the feed medium is fed at multiple stages, the compositions of the feed media fed at the various stages can be the same or different.

The culture can be performed as an aeration culture at a fermentation temperature of 20 to 45° C., or at 30 to 42° C. in another example. As for the gas supplied to the fermentation tank, high concentration oxygen can be supplied simultaneously with air, and thereby the oxygen concentration in the supply gas can be elevated, as well as air (refer to Japanese Patent Publication (KOKOKU) Nos. 05-048117 and 5-39594).

The amount of oxygen supplied can be such that the oxygen concentration in the medium is 2 to 4 ppm, and a mixed gas of high concentration oxygen of 40 to 100% oxygen concentration and air can be supplied at 1/10 to 1.5/1 vvm. The high concentration oxygen can be prepared by using an oxygen concentrator. As the oxygen concentrator, there are the PSA type and oxygen enrichment membrane type, and a method of evaporating liquid oxygen with an evaporator and supplying it to a fermentation tank, or directly supplying liquid oxygen to a fermentation tank, can be used.

The aeration culture is performed with the pH adjusted to 5 to 9. If pH drops during the culture, for example, calcium carbonate or an alkali such as ammonia gas and aqueous ammonia can be added to neutralize the culture. When the target amino acid is an acidic amino acid, for example, L-glutamic acid, the culture can be performed at pH 3 to 9, or pH 3 to 5 in another example. When the culture is performed under such conditions, for example, for about 10 to 120 hours, a marked amount of target substance accumulates in the culture medium. Although the concentration of target substance which accumulates is not limited so long as it is higher than that observed with wild-type strains and the target substance can be collected from the medium, it can be 50 g/L or higher, or in another example, 75 g/L or higher, or in another example, 100 g/L or higher when the target substance is an L-amino acid. It can be 50 g/L or higher, or in another example, 75 g/L or higher, or in another example, 100 g/L or higher, when the target substance is a nucleic acid.

The target substance can be collected according to a known collection method from the culture medium after the culture. For example, the target substance which has precipitated in the medium can be collected by centrifugation or filtration. Moreover, the target substance which is dissolved in the medium can be crystallized, and then the precipitated target substance and the crystals can be isolated together.

The culture of the microorganism can be performed as a seed culture and main culture in order to ensure production of more target substance than a certain level. For example, the seed culture can be performed as a shaking culture using a flask or the like, or a batch culture, and the main culture can be performed as a fed-batch culture or a continuous culture. Alternatively, both the seed culture and the main culture can be performed as batch culture. Furthermore, prior to the seed culture and the main culture, a pre-culture can be performed once or twice or more times to successively make the culture scale larger.

In these culture methods, when the target substance concentration reaches the intended level, a part of the target substance can be extracted, and fresh medium can be added to repeat the culture. As fresh medium, a medium containing a carbon source and a nutrient having a growth promoting effect (growth promoting factor) is an example. As the carbon source, glucose, sucrose, and fructose are examples. As the growth promoting factor, nitrogen sources, phosphoric acid, amino acids, and so forth are examples. As the nitrogen source, ammonia, ammonium salts such as ammonium sulfate, ammonium carbonate, ammonium chloride, ammonium phosphate and ammonium acetate, urea, nitrates, and so forth can be used. Furthermore, as the phosphoric acid source, potassium dihydrogenphosphate and dipotassium hydrogen-phosphate can be used. As for the amino acids, when an auxotrophic mutant strain is used, the required nutrient can be supplemented.

When a fed-batch culture or continuous culture is performed, the feed medium can be intermittently fed so that the supply of saccharide or nutrition source is temporarily suspended. The supply of the feed medium is suspended, for example, at maximum, 30% or less, 20% or less in another example, 10% or less in another example, of the feeding time. When the feed medium is intermittently fed, the feed medium can be added over a predetermined time period, and the second and following addition periods can be controlled to begin when the pH increases or the dissolved oxygen concentration is detected by a computer upon depletion of the carbon source In this way, the substrate concentration in the culture tank is always automatically maintained at a low level (U.S. Pat. No. 5,912,113).

As the carbon source, glucose, sucrose, and fructose are examples. As the growth promoting factor, nitrogen sources, phosphoric acid, amino acids, and so forth are examples. As the nitrogen source, ammonia, ammonium salts such as ammonium sulfate, ammonium carbonate, ammonium chloride, ammonium phosphate and ammonium acetate, urea, nitrates, and so forth can be used. Furthermore, as the phosphoric acid source, potassium dihydrogenphosphate and dipotassium hydrogenphosphate can be used. As for the amino acids, when an auxotrophic mutant strain is used, the required nutrient can be supplemented. Furthermore, the feed medium can be one type of medium, or a mixture of two or more types of media. When two or more types of feed media are used, the media can be mixed and fed by using one feed can, or the media can be separately fed by using two or more feed cans.

When a fed-batch culture is performed, the amount of feed medium can be in such an amount that the saccharide amount in the feed medium or the whole fermentation medium does not exceed 30 g/L, and it can be controlled to be 20 g/L or lower, or 10 g/L or lower in another example. In particular, the saccharide concentration can be controlled so that it is in the aforementioned concentration range at the end of the logarithmic proliferation of the microorganism and thereafter. The feed rate of the carbon source can be controlled by using the method described in U.S. Pat. No. 5,912,113. Furthermore, saccharide and phosphoric acid can be fed at such concentrations so that the saccharide and phosphoric acid serve as limiting factors of the bacterial cell growth. Phosphoric acid can be present in the feed medium in an amount of 2 or lower, 1.5 or lower in another example, 1 or lower in another example, expressed in terms of the phosphorous/carbon (P/C) ratio (refer to U.S. Pat. No. 5,763,230).

When the continuous culture method is used, the medium can be extracted and fed simultaneously, or a part of the medium can be extracted, and then the medium can be fed. Furthermore, the method can also be a continuous culture method such as by recycling the cells extracted from the culture medium containing a target substance, and only the cells are returned to the fermenter (French Patent No. 2669935). As the method for continuously or intermittently feeding a nutrient source, the same method as used in the fed-batch culture can be used.

When the culture medium is intermittently extracted, some of the target substance is extracted when the target substance concentration reaches a predetermined level, and fresh medium is fed to continue the culture. Furthermore, the culture can be performed so that the final volume of the medium after adding the medium is equal to the volume of the culture medium before the extraction. The term "equal" means that the volume corresponds to about 93 to 107% of the volume of the medium before the extraction.

When the culture medium is continuously extracted, the extraction is desirably started at the same time as or after the feeding of the nutrient medium. For example, within 5 hours at maximum, desirably 3 hours, more desirably 1 hour, after the start of the feeding, the extraction can be started. Furthermore, the extraction volume of the culture medium can be equal to the volume of the fed medium.

The continuous culture method of recycling bacterial cells includes intermittently or continuously extracting the fermentation medium when the target substance concentration reaches a predetermined level, extracting only the target substance, and re-circulating filtration residues containing bacterial cells into the fermentation vessel, and it can be performed by referring to, for example, French Patent No. 2669935.

Furthermore, the crystals precipitated by the crystallization method can be extracted from the fermentation tank during the culture. Specifically, a method of increasing productivity by performing fermentation in a fermentation tank can be used, extracting the fermentation broth containing the target substance and cells from the fermentation broth, collecting crystals of the target substance by centrifugation or concentration, and recycling the fermentation broth to the fermentation tank. For example, in the apparatus shown in FIG. 1, a method of circulating fermentation broth containing the target substance and cells via the line A, concentrating crystals of the target substance by centrifugation B, extracting the crystals from the line C, and recycling the fermentation broth to the fermentation tank via the line D. In this method, the cells may be or may not be recycled back into the fermentation tank. For the centrifugation of the crystals, a liquid cyclone can be used (Japanese Patent Laid-open No. 5-92944).

Furthermore, for the production of a nucleic acid, by allowing purine nucleoside phosphorylase and phosphoribosyltransferase to act on inosine or guano sine prepared by an exemplary method of the present invention, 5'-inosinic acid or 5'-guanylic acid can be obtained.

Moreover, it is also possible to phosphorylate the purine nucleoside produced using an exemplary microorganism of the present invention by allowing phosphotransferase to act on the purine nucleoside to produce a purine nucleotide (nucleoside 5'-phosphoric acid ester) (Japanese Patent Laid-open No. 2000-295996). For example, the method for producing a purine nucleotide using an *Escherichia* bacterium into which a gene encoding inosine guanosine kinase of *Escherichia coli* is introduced (WO91/08286), and the method for producing a purine nucleotide using *Corynebacterium ammoniagenes* into which a gene encoding inosine guanosine kinase of *Exiguobacterium acetylicum* is introduced (WO96/30501) can be used.

Moreover, it is also possible to produce a purine nucleotide (nucleoside 5'-phosphoric acid ester) by allowing a microorganism which is able to produce a nucleoside 5'-phosphoric acid ester or acid phosphatase (EC 3.1.3.2) to act on the purine nucleoside produced by using an exemplary microorganism of the present invention and a phosphate donor, such as polyphosphoric acid, phenyl phosphate, and carbamyl phosphate. Although the microorganism able to produce a nucleoside 5'-phosphoric acid ester is not particularly limited, so long as it can convert a purine nucleoside into a purine nucleotide, and, examples include the microorganism disclosed in International Patent Publication WO96/37603.

Moreover, *Escherichia blattae* JCM 1650, *Serratia ficaria* ATCC 33105, *Klebsiella planticola* IFO 14939 (ATCC 33531), *Klebsiella pneumoniae* IFO 3318 (ATCC 8724), *Klebsiella terrigena* IFO 14941 (ATCC 33257), *Morganella morganii* IFO 3168, *Enterobacter aerogenes* IFO 12010, *Enterobacter aerogenes* IFO 13534 (ATCC 13048), *Chromobacterium fluviatile* IAM 13652, *Chromobacterium violaceum* IFO 12614, *Cedecea lapagei* JCM 1684, *Cedecea davisiae* JCM 1685, *Cedecea neteri* JCM 5909, and so forth disclosed in Japanese Patent Laid-open No. 07-231793 can also be used.

As the acid phosphatase, for example, those disclosed in Japanese Patent Laid-open No. 2002-000289 can be used, as well as an acid phosphatase with increased affinity to a nucleoside (Japanese Patent Laid-open No. 10-201481), a mutant acid phosphatase with decreased nucleotidase activity (WO96/37603), a mutant acid phosphatase with decreased phosphoric acid ester hydrolysis activity (Japanese Patent Laid-open No. 2001-245676) and so forth.

It is also possible to obtain a purine nucleotide by chemically phosphorylating a purine nucleoside produced using an exemplary microorganism of the present invention (Bulletin of the Chemical Society of Japan, 42, 3505). Moreover, a method of obtaining GMP by coupling the microorganism with an XMP-producing ability and XMP aminase activity using the ATP-regenerating system of a microorganism, and a method of obtaining IMP by coupling inosine kinase (Biosci. Biotech. Biochem., 51, 840 (1997); Japanese Patent Laid-open No. 63-230094) can also be used.

Inosine, guanosine, or purine nucleosides prepared by an exemplary method of the present invention can be a purified product, or a purine nucleoside fermentation broth, or a crude product containing a purine nucleoside.

<2> Microorganisms

The microorganism is not particularly limited, so long as it is a microorganism which is able to produce an L-amino acid or nucleic acid, and also able to produce the L-amino acid or nucleic acid in a liquid medium when it is cultured in the medium. The amount of the L-amino acid or nucleic acid to be produced is also not particularly limited so long as it can be produced in such an amount that it can be collected from the medium. However, the microorganism be able to crystallize the target substance in the medium, and the microorganism can produce the target substance, for example, at a concentration higher than the concentrations described in Tables 1 and 2.

For example, when the pH of an aqueous solution containing L-glutamic acid is reduced, the solubility of L-glutamic acid markedly decreases around pKa (4.25) of the γ-carboxyl group, and is the lowest at the isoelectric point (pH 3.2). Although it also depends on the medium composition, L-glutamic acid usually dissolves in an amount of 10 to 20 g/L at pH 3.2, 30 to 40 g/L at pH 4.0, and 50 to 60 g/L at pH 4.7, at about 30° C.

Exemplary microorganisms of the present invention, or a parent strain which is used to derive an exemplary microorganism, include microorganisms belonging to the family Enterobacteriaceae, typical examples of which are *Escherichia* bacteria and *Pantoea* bacteria, coryneform bacteria, and so forth. In addition, methanol-utilizing bacteria such as *Methylophilus* bacteria and *Methylobacillus* bacteria, which can produce L-amino acid from methanol, can also be used. Further examples of microorganisms belonging to the family Enterobacteriaceae include enterobacteria belonging to γ-proteobacteria such as those belonging to the genus *Enterobacter, Klebsiella, Serratia, Erwinia, Salmonella, Morganella*, or the like, and examples of other microorganisms include *Alicyclobacillus* bacteria, *Bacillus* bacteria, yeasts belonging to the genus *Saccharomyces, Candida* or the like, and so forth.

As the *Escherichia* bacteria, those mentioned in the work of Neidhardt et al. (Neidhardt, F. C. et al., *Escherichia coli and Salmonella Typhimurium*, American Society for Microbiology, Washington D.C., 1208, table 1), such as *Escherichia coli*, can be utilized. Examples of wild-type strains of *Escherichia coli* include, for example, the K12 strain and derivatives thereof, *Escherichia coli* MG1655 strain (ATCC No. 47076), W3110 strain (ATCC No. 27325), and so forth. They are available from the American Type Culture Collection (ATCC, Address: P.O. Box 1549, Manassas, Va. 20108, United States of America). That is, registration numbers are given to each of the strains, and the strains can be ordered by using these registration numbers. The registration numbers of the strains are listed in the catalogue of the American Type Culture Collection (refer to http://www.atcc.org/).

Furthermore, examples of the *Enterobacter* bacteria include *Enterobacter agglomerans, Enterobacter aerogenes* and so forth, and examples of the *Pantoea* bacteria include *Pantoea ananatis*. Some species of *Enterobacter agglomerans* have been recently re-classified into *Pantoea agglomerans, Pantoea ananatis, Pantoea stewartii* or the like, based on the nucleotide sequence analysis of 16S rRNA, etc. Both of the *Enterobacter* bacteria and *Pantoea* bacteria can be used so long as the chosen bacterium is classified into the family Enterobacteriaceae. When a *Pantoea ananatis* strain is bred by a genetic engineering technique, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

Specific examples of the *Methylophilus* bacteria include *Methylophilus methylotrophus*, and typical examples of *Methylophilus methylotrophus* include the AS1 strain (NCIMB 10515) and so forth. The *Methylophilus methylotrophus* AS1 strain is available from the National Collections of Industrial and Marine Bacteria (Address: NCIMB Lts., Tony Research Station, 135, Abbey Road, Aberdeen AB9 8DG, United Kingdom).

Specific examples of the *Methylobacillus* bacteria include *Methylobacillus glycogenes, Methylobacillus flagellatum*, and so forth. Examples of *Methylobacillus glycogenes* include the T-11 strain (NCIMB 11375), ATCC 21276 strain, ATCC 21371 strain, ATR80 strain (described in Appl. Microbiol. Biotechnol., vol. 42, pp. 67-72, 1994), A513 strain (described in Appl. Microbiol. Biotechnol., vol. 42, pp. 67-72 (1994)), and so forth. The *Methylobacillus glycogenes* NCIMB 11375 strain can be obtained from the National Collections of Industrial and Marine Bacteria (Address: NCIMB Lts., Tony Research Station 135, Abbey Road, Aberdeen AB9 8DG, United Kingdom). Examples of *Methylobacillus flagellatum* include the KT strain (described in Arch. Microbiol., vol. 149, pp. 441-446, 1988) and so forth.

The coryneform bacteria are a group of microorganisms defined in Bergey's Manual of Determinative Bacteriology, 8th Ed., p. 599 (1974), and microorganisms classified into such aerobic, Gram-positive and nonacid-fast bacilli which are unable to sporulate can be used. The coryneform bacteria include bacteria which have previously been classified into the genus *Brevibacterium* but are presently united into the genus *Corynebacterium* (Int. J. Syst. Bacteriol. 41:255-260 (1991)), and bacteria belonging to the genus *Brevibacterium* or *Microbacterium*, which are closely related to the genus *Corynebacterium*.

Specific examples of such coryneform bacteria include the following:
*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum*
*Brevibacterium roseum*
*Brevibacterium saccharolyticum*
*Brevibacterium thiogenitalis*
*Corynebacterium ammoniagenes*
*Brevibacterium album*
*Brevibacterium cerinum*
*Microbacterium ammoniaphilum*

Specific examples of these bacteria include the following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060
*Corynebacterium lilium* ATCC 15990
*Corynebacterium melassecola* ATCC 17965
*Corynebacterium efficiens* AJ12340 (FERM BP-1539)
*Corynebacterium herculis* ATCC 13868
*Brevibacterium divaricatum* ATCC 14020
*Brevibacterium flavum* ATCC 13826, ATCC 14067, AJ12418 (FERM BP-2205)
*Brevibacterium immariophilum* ATCC 14068
*Brevibacterium lactofermentum* ATCC 13869 (*Corynebacterium glutamicum* TCC 13869)
*Brevibacterium roseum* ATCC 13825
*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerinum* ATCC 15112
*Microbacterium ammoniaphilum* ATCC 15354

These strains are available from, for example, the American Type Culture Collection (ATCC) (Address: P.O. Box 1549, Manassas, Va. 2010812301 Parklawn Drive, Rockville, Md. 20852, United States of America). The AJ12340 strain was deposited on Oct. 27, 1987 in National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-5466, Japan), with a deposit number of FERM BP-1539 under the provisions of Budapest Treaty. The AJ12418 strain was deposited on Jan. 5, 1989 in National Institute of Bioscience and Human Technology of Agency of Industrial Science and Technology, with a deposit number of FERM BP-2205 under the provisions of the Budapest Treaty.

When *Bacillus* bacteria are used, examples thereof include *Bacillus subtilis, Bacillus amyloliquefaciens, Bacillus pumilus*, and so forth.

Examples of *Bacillus subtilis* include *Bacillus subtilis* 168 Marburg strain (ATCC 6051), *Bacillus subtilis* PY79 strain (Plasmid, 1984, 12, 1-9), and so forth. Examples of *Bacillus amyloliquefaciens* include *Bacillus amyloliquefaciens* T strain (ATCC 23842), *Bacillus amyloliquefaciens* N strain (ATCC 23845), and so forth. Examples of *Bacillus pumilus* include *Bacillus pumilus* Gottheil No. 3218 (ATC 21005) (U.S. Pat. No. 3,616,206), and so forth.

Hereinafter, methods for imparting an L-amino acid- or nucleic acid-producing ability to parent strains as mentioned above are described.

To impart the ability to produce an L-amino acid or a nucleic acid, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include by acquiring an auxotrophic mutant, an analogue-resistant strain, or a metabolic regulation mutant, or constructing a recombinant strain so that it overexpresses an L-amino acid or nucleic acid biosynthesis enzyme. Here, in the breeding of an L-amino acid-producing bacteria, one or more of the above-described properties such as auxotrophy, analogue-resistance, or metabolic regulation mutation can be imparted. Expression of one or more L-amino acid biosynthesis enzymes can be enhanced. Furthermore, the methods of imparting properties such as an auxotrophic mutation, analogue resistance, or metabolic regulation mutation can be combined with the methods of enhancing the biosynthesis enzymes.

An auxotrophic mutant strain, L-amino acid or nucleic acid analogue-resistant strain, or metabolic regulation mutant strain with an ability to produce an L-amino acid or nucleic acid can be obtained by subjecting a parent strain or wild-type strain to a conventional mutagenesis, such as exposure to X-rays or UV irradiation, or treatment with a mutagen such as N-methyl-N'-nitro-N-nitrosoguanidine, etc., and then selecting from the obtained mutant stains those which exhibit an autotrophy, analogue resistance, or metabolic regulation mutation and which also have the ability to produce an L-amino acid or nucleic acid.

An auxotrophic mutant strain, L-amino acid analogue-resistant strain, or metabolic regulation mutant strain with an ability to produce an L-amino acid can be obtained by subjecting a parent strain or wild-type strain to a conventional mutagenesis, such as exposure to X-rays or UV irradiation, or treatment with a mutagen such as N-methyl-N'-nitro-N-nitrosoguanidine or ethyl methanesulfonate (EMS), etc., and then selecting from the obtained mutant stains those which exhibit an autotrophy, analogue resistance, or metabolic regulation mutation and which also have the ability to produce an L-amino acid.

Methods for imparting L-amino acid-producing ability and amino acid-producing bacteria will be specifically exemplified below.

L-Tryptophan, L-phenylalanine, and L-tyrosine are all aromatic amino acids and share a common biosynthesis pathway. Examples of the genes encoding the biosynthesis enzymes for these aromatic amino acids include deoxyarabino-heptulosonate phosphate synthase (aroG), 3-dehydroquinate synthase (aroB), shikimic acid dehydrogenase (aroE), shikimate kinase (aroL), 5-enolpyruvylshikimate-3-phosphate synthase (aroA), and chorismate synthase (aroC) (European Patent Laid-open No. 763127). It is known that these genes are controlled by the tyrosine repressor (tyrR), so activity of an aromatic amino acid biosynthesis enzyme can also be increased by deleting the tyrR gene (see European Patent Laid-open No. 763127). The abbreviations in parentheses after the enzyme names represent the gene names (the same shall apply hereafter).

In order to enhance the productivity of each of the target aromatic amino acids, biosynthesis of an amino acid other than the target amino acid can be attenuated. For example, when the target amino acid is L-tryptophan, biosynthetic pathways of L-phenylalanine and/or L-tyrosine can be attenuated (U.S. Pat. No. 4,371,614).

Furthermore, 3-deoxy-D-arabinoheptulosonate-7-phosphate synthetase (aroF, aroG) is subject to feedback inhibition by aromatic amino acids. Therefore, the enzyme can be modified so that it is not subject to the feedback inhibition. An aromatic L-amino acid-producing bacterium can be obtained, for example, by introducing a mutant aroF in which the L-aspartic acid at position 147 or the L-serine at position 181 is replaced by another amino acid, or by introducing a mutant aroG gene in which the L-aspartic acid at position 146 from the N-terminus, the L-methionine at position 147, the L-proline at position 150 or the L-alanine at position 202, or both the L-methionine at position 157 and the L-alanine at position 219 are replaced by other amino acid(s) (European Patent Laid-open No. 0488424).

An example of a gene involved in the synthesis of branched chain amino acids is the ilvGMEDA operon, and this operon is subject to expression control (attenuation) by L-valine and/or L-isoleucine and/or L-leucine. Therefore, productivity of a microorganism for these L-amino acids can be improved by introducing into the microorganism the ilvGMEDA operon in which the region required for attenuation is removed or mutated.

Aromatic amino acids and branched chain amino acids share a common biosynthesis system, and therefore a strain in which a biosynthesis system specific for an aromatic amino acid or branched chain amino acid other than the target L-amino acid is attenuated can be used. For example, a strain which can efficiently produce a target L-amino acid can be obtained by attenuating the biosynthesis system of L-phenylalanine and L-tyrosine when the target amino acid is L-tryptophan, attenuating the biosynthesis system of L-tryptophan and L-tyrosine when the target amino acid is L-phenylalanine, attenuating the biosynthesis system of L-leucine and L-isoleucine when the target amino acid is L-valine, attenuating the biosynthesis system of L-valine and L-leucine when the target amino acid is L-isoleucine, or attenuating the biosynthesis system of L-valine and L-isoleucine when the target amino acid is L-leucine. Attenuation of a biosynthesis system can be attained by introducing a mutation into a gene coding for an enzyme of the biosynthesis system or obtaining a strain which requires the L-amino acid synthesized by the biosynthesis system to be attenuated using a synthetic medium containing that L-amino acid.

Methods for imparting L-amino acid-producing ability and microorganisms to which L-amino acid-producing ability is imparted, and which can be used for the present invention are exemplified below.

L-Tryptophan-producing Bacteria

Examples of L-tryptophan-producing bacteria and parent strains which can be used to derive them include, but are not limited to, strains belonging to the genus *Escherichia*, such as *E. coli* JP4735/pMU3028 (DSM10122) and JP6015/pMU91 (DSM10123) which are deficient in tryptophanyl-tRNA synthetase encoded by mutant trpS gene (U.S. Pat. No. 5,756,345), *E. coli* SV164 (pGH5) having a serA allele encoding phosphoglycerate dehydrogenase not subject to feedback inhibition by serine and a trpE allele encoding anthranilate synthase not subject to feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614), *E. coli* AGX17/pGX50, pACKG4-pps in which a phosphoenolpyruvate-producing ability is enhanced (WO97/08333, U.S. Pat. No. 6,319,696), and so forth. L-Tryptophan-producing bacteria belonging to the genus *Escherichia* which have enhanced activity of the protein encoded by the yedA or yddG gene can also be used (U.S. Patent Published Applications 2003/0148473 A1 and 2003/0157667 A1).

Examples of L-tryptophan-producing bacteria and parent strains which can be used to derive them also include strains in which one or more activities of the following enzymes are enhanced: anthranilate synthase (trpE), phosphoglycerate dehydrogenase (serA), and tryptophan synthase (trpAB). The anthranilate synthase and phosphoglycerate dehydrogenase both are subject to feedback inhibition by L-tryptophan and L-serine, therefore a mutation desensitizing the feedback inhibition can be introduced into these enzymes. Specific examples of strains having such a mutation include *E. coli* SV164 which harbors desensitized anthranilate synthase and a transformant strain SV164(pGH5) obtained by introducing into the *E. coli* SV164 the plasmid pGH5, which contains a mutant serA gene encoding a feedback inhibition-desensitized phosphoglycerate dehydrogenase.

Examples of L-tryptophan-producing bacteria and parent strains which can be used to derive them also include a strain which has enhanced activity of 3-phosphoserine phosphatase (serB) (U.S. Pat. No. 4,371,614), a strain which has enhanced activity of phosphoenolpyruvate carboxykinase (pckA) (WO2004/090125), and a strain which constitutively expresses the maleate synthase-isocitrate lyase-isocitrate dehydrogenase-kinase/phosphatase operon (ace operon) or in which expression of this operon is enhanced (WO2005/103275).

Examples of L-tryptophan-producing bacteria and parent strains for deriving them also include strains into which the tryptophan operon containing a gene encoding inhibition-desensitized anthranilate synthase has been introduced (Japanese Patent Laid-open Nos. 57-71397, 62-244382, U.S. Pat. No. 4,371,614). Moreover, L-tryptophan-producing ability can be imparted by enhancing expression of a gene which encodes tryptophan synthase in the tryptophan operon (trpBA). Tryptophan synthase consists of α and β subunits which are encoded by the trpA and trpB genes, respectively. In addition, L-tryptophan-producing ability can be improved by enhancing expression of the isocitrate lyase-malate synthase operon (WO2005/103275).

As coryneform bacteria, *Corynebacterium glutamicum* AJ12118 (FERM BP-478, Japanese Patent No. 01681002), which is resistant to sulfaguanidine, the coryneform bacterium introduced with the tryptophan operon (Japanese Patent Laid-open No. 63-240794), and the coryneform bacterium introduced with a gene coding for shikimate kinase derived from a coryneform bacterium (Japanese Patent Laid-open No. 01-994749) can be used.

L-Phenylalanine-producing Bacteria

Examples of L-phenylalanine-producing bacteria and parent strains which can be used to derive them include, but are not limited to, strains belonging to the genus *Escherichia*, such as *E. coli* AJ12739 (tyrA::Tn10, tyrR) (VKPM B-8197), *E. coli* HW1089 (ATCC 55371) harboring a mutant pheA34 gene (U.S. Pat. No. 5,354,672), *E. coli* MWEC101-b (Korean Patent No. 8903681), *E. coli* NRRL B-12141, NRRL B-12145, NRRL B-12146, and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ12604 (FERM BP-3579) can be used (European Patent Publication No. 488424 B1). Furthermore, L-phenylalanine-producing bacteria belonging to the genus *Escherichia* with an enhanced activity of the protein encoded by the yedA gene or the yddG gene can also be used (U.S. Patent Published Applications No. 2003/0148473 A1 and 2003/0157667 A1).

As phenylalanine-producing coryneform bacteria, the *Cornebacterium glutamicum* BPS-13 (FERM BP-1777), K77 (FERM BP-2062), and K78 (FERM BP-2063) (European Patent Laid-open No. 331145, Japanese Patent Laid-open No. 02-303495), of which phosphoenolpyruvate carboxylase or pyruvate kinase activity is reduced, tyrosine-auxotrophic strain (Japanese Patent Laid-open No. 05-049489), and so forth can be used.

A bacterium which efficiently produces phenylalanine can also be obtained by modifying a bacterium so that the it incorporates by-products, for example, by increasing the expression of the L-tryptophan uptake gene, tnaB or mtr, or the L-tyrosine uptake gene, tyrP (European Patent No. 1484410).

L-Tyrosine-producing Bacteria

Examples of tyrosine-producing bacteria include *Escherichia* bacteria with a desensitized prephenate dehydratase gene (tyrA). The expression product of this gene is desensitized to inhibition by tyrosine (European Patent Application Laid-open No. 1616940).

L-Valine-producing Bacteria

Examples of L-valine-producing bacteria and parent strains which can be used to derive L-valine-producing bacteria include, but are not limited to, strains which have been modified to overexpress the ilvGMEDA operon (U.S. Pat. No. 5,998,178). The region in the ilvGMEDA operon which is required for attenuation can be removed so that expression of the operon is not attenuated by the L-valine that is produced. Furthermore, the ilvA gene in the operon can be disrupted so that threonine deaminase activity is decreased.

Examples of L-valine-producing bacteria which can be used to derive L-valine-producing bacteria also include mutant strains with amino-acyl t-RNA synthetase having a mutation (U.S. Pat. No. 5,658,766). For example, *E. coli* VL1970, which has a mutation in the ileS gene encoding isoleucine tRNA synthetase, can be used. *E. coli* VL1970 was deposited at the Russian National Collection of Industrial Microorganisms (VKPM) (1 Dorozhny proezd., 1 Moscow 117545, Russia) on Jun. 24, 1988 under an accession number VKPM B-4411.

Furthermore, mutants requiring lipoic acid for growth and/or lacking H$^+$-ATPase can also be used as parent strains (WO96/06926).

Examples of L-valine-producing bacteria of coryneform bacteria include, for example, strains modified so that expression of a gene encoding an L-valine biosynthetic enzyme is enhanced. Examples of the L-valine biosynthesis enzyme include enzymes encoded by genes present on the ilvBNC operon, that is, acetohydroxy acid synthetase encoded by ilvBN and isomero-reductase encoded by ilvC (WO00/50624). Since the ilvBNC operon is subject to expression regulation by L-valine and/or L-isoleucine and/or L-leucine, it is desirable to eliminate attenuation to avoid expression suppression by L-valine that is produced.

Impartation of L-valine-producing ability to coryneform bacteria can be performed by decreasing or eliminating activity of at least one kind of enzyme which is involved in a metabolic pathway that decreases L-valine production. For example, decrease of the activity of threonine dehydratase involved in the L-leucine synthesis, or activity of an enzyme that involved in D-panthothenate synthesis is contemplated (WO00/50624).

Examples of methods for imparting L-valine-producing ability also include imparting resistance to an amino acid analogue or the like.

Examples include, for example, mutant strains which are auxotrophic for L-isoleucine and L-methionine, and resistant to D-ribose, purine ribonucleoside or pyrimidine ribonucleoside, and have an ability to produce L-valine (FERM P-1841, FERM P-29, Japanese Patent Publication No. 53-025034), mutant strains resistant to polyketides (FERM P-1763, FERM P-1764, Japanese Patent Publication No. 06-065314), and mutant strains resistant to L-valine in a medium containing acetic acid as the sole carbon source and sensitive to pyruvic acid analogues (fluoropyruvic acid etc.) in a medium containing glucose as the sole carbon source (FERM BP-3006, BP-3007, Japanese Patent No. 3006929).

L-Isoleucine-producing Bacteria

Examples of L-isoleucine-producing bacteria and parent strains which can be used to derive L-isoleucine-producing bacteria include, but are not limited to, mutants having resistance to 6-dimethylaminopurine (Japanese Patent Laid-open No. 5-304969), mutants having resistance to an isoleucine analogue such as thiaisoleucine and isoleucine hydroxamate, and mutants additionally having resistance to DL-ethionine and/or arginine hydroxamate (Japanese Patent Laid-open No. 5-130882). In addition, recombinant strains transformed with genes encoding proteins involved in L-isoleucine biosynthesis, such as threonine deaminase and acetohydroxy acid synthase, can also be used as parent strains (Japanese Patent Laid-open No. 2-458, French Patent No. 0356739, and U.S. Pat. No. 5,998,178).

Examples of L-isoleucine-producing strains of coryneform bacteria include the coryneform bacterium in which the brnE gene coding for a branched chain amino acid excretion protein is amplified (Japanese Patent Laid-open No. 2001-169788), the coryneform bacterium imparted with L-isoleucine-producing ability by protoplast fusion with an L-lysine-producing bacterium (Japanese Patent Laid-open No. 62-74293), the coryneform bacterium in which homoserine dehydrogenase is enhanced (Japanese Patent Laid-open No. 62-91193), the threonine hydroxamete resistant strain (Japanese Patent Laid-open No 62-195293), α-ketomalonic acid resistant strain (Japanese Patent Laid-open No. 61-15695), and the methyl lysine resistant strain (Japanese Patent Laid-open No. 61-15696).

L-Leucine-producing Bacteria

Examples of L-leucine-producing bacteria and parent strains for deriving L-leucine-producing bacteria include, but are not limited to, *Escherichia* bacteria, such as *E. coli* strains resistant to leucine (for example, the strain 57 (VKPM B-7386, U.S. Pat. No. 6,124,121)) or leucine analogues including β-2-thienylalanine, 3-hydroxyleucine, 4-azaleucine and 5,5,5-trifluoroleucine (Japanese Patent Publication No. 62-34397 and Japanese Patent Laid-open No. 8-70879); *E. coli* strains obtained by the genetic engineering method described in WO96/06926; and *E. coli* H-9068 (Japanese Patent Laid-open No. 8-70879).

The bacterium can also be improved by enhancing the expression of one or more genes involved in L-leucine biosynthesis. Examples of such genes include genes of the leuABCD operon, which can be represented by a mutant leuA gene coding for isopropylmalate synthase desensitized to feedback inhibition by L-leucine (U.S. Pat. No. 6,403,342).

In addition, the bacterium can be improved by enhancing the expression of one or more genes coding for proteins which excrete one or more L-amino acids from the bacterial cell. Examples of such genes include the b2682 and b2683 genes (ygaZH genes) (European Patent Laid-open No. 1239041 A2).

Examples of L-leucine-producing strains of coryneform bacteria include the 2-thiazolealanine and β-hydroxyleucine-resistant strains (Japanese Patent Laid-open No. 8-266295), the valine analogue-resistant strain (Japanese Patent Laid-open No. 63-248392), the valine auxotrophic strain (Japanese Patent Publication No. 38-4395), the S-(2-aminoethyl)-L-cysteine (AEC) resistant strain (Japanese Patent Publication No. 51-37347), and the phenylalanine, valine and isoleucine auxotrophic strain (Japanese Patent Publication No. 54-36233).

L-Glutamic Acid-producing Bacteria

Examples of L-glutamic acid-producing bacteria include strains in which expression of a gene encoding an L-glutamic acid biosynthetic enzyme is enhanced. Examples of such genes include, but are not limited to, genes encoding glutamate dehydrogenase (gdhA), glutamine synthetase (glnA), glutamate synthetase (ghAB), isocitrate dehydrogenase (icdA), aconitate hydratase (acnA, acnB), citrate synthase (ghA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), triose phosphate isomerase (tpiA), fructose bisphosphate aldolase (fbp), phosphofructokinase (pfkA, pfkB), glucose phosphate isomerase (pgi), methylcitrate synthase (prpC) and so forth.

Examples of strains which have been modified so that expression of the citrate synthetase gene, the phosphoenolpyruvate carboxylase gene, the isocitrate dehydrogenase gene, the pyruvate dehydrogenase gene, and/or the glutamate dehydrogenase gene is enhanced include those disclosed in European Patent Laid-open Nos. 1078989, 955368, and 952221.

The modification for imparting L-glutamic acid producing ability can be attained by decreasing or eliminating activity of an enzyme that catalyzes a reaction branching off from the L-glutamic acid biosynthesis pathway and producing a compound other than L-glutamic acid. Examples of such an enzyme that catalyzes a reaction branching off from the L-glutamic acid biosynthesis pathway and producing a compound other than L-glutamic acid include isocitrate lyase (aceA), α-ketoglutarate dehydrogenase (sucA), acetohydroxy acid synthase (ilvG), acetolactate synthase (ilvI), formate acetyltransferase (pfl), lactate dehydrogenase (ldh), glutamate decarboxylase (gadAB), 1-pyrroline-5-carboxylate dehydrogenase (putA), and so forth.

For example, in order to decrease the α-ketoglutarate dehydrogenase activity, a modification can be performed by using the sucA (odhA) gene coding for the E1o subunit of the enzyme. Examples of strains with decreased α-ketoglutarate dehydrogenase activity include, for example, the following strains:

*Brevibacterium lactofermentum* ΔS strain (WO95/34672)
*Brevibacterium lactofermentum* AJ12821 (FERM BP-4172; French Patent No. 9401748)
*Brevibacterium flavum* AJ12822 (FERM BP-4173; French Patent No. 9401748)
*Corynebacterium glutamicum* (FERM BP-4174; French Patent No. 9401748)

Pantoea ananatis AJ13601 (FERM BP-7207)
Klebsiella planticola AJ13410 (FERM BP-6617)
Pantoea ananatis AJ13355 (FERM BP-6614)
Pantoea ananatis AJ13356 is deficient in α-ketoglutarate dehydrogenase activity as a result of disruption of the αKGDH-E1 subunit gene (sucA). This strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, it is described as *Pantoea ananatis* in this specification.

Furthermore, the ability to produce L-glutamic acid in coryneform bacteria can also be achieved by a method of amplifying the yggB gene (NCgl 1221; NP_600492. Reports small-conductance. [gi:19552490], WO2006/070944), and a method of introducing a mutant yggB gene in which a mutation is introduced into the coding region.

The microorganism can be a microorganism modified so that D-xylose-5-phosphate phosphoketolase activity and/or fructose-6-phosphate phosphoketolase activity is enhanced.

Either one or both of the D-xylose-5-phosphate phosphoketolase activity and fructose-6-phosphate phosphoketolase activity can be activated.

Examples of other methods for imparting or enhancing L-glutamic acid-producing ability include a method of imparting resistance to an organic acid analogue, a respiratory chain inhibitor, etc., and a method of imparting sensitivity to a cell wall synthesis inhibitor. Examples of such methods include the methods of imparting resistance to monofluoroacetic acid (Japanese Patent Laid-open No. 50-113209), the method of resistance to adenine or thymine (Japanese Patent Laid-open No. 57-065198), the method of attenuating urease (Japanese Patent Laid-open No. 52-038088), the method of imparting resistance to malonic acid (Japanese Patent Laid-open No. 52-038088), the method of imparting resistance to benzopyrones or naphthoquinones (Japanese Patent Laid-open No. 56-1889), the method of imparting resistance to HOQNO (Japanese Patent Laid-open No. 56-140895), the method of imparting resistance to α-ketomalonic acid (Japanese Patent Laid-open No. 57-2689), the method of imparting resistance to guanidine (Japanese Patent Laid-open No. 56-35981), the method of imparting sensitivity to penicillin (Japanese Patent Laid-open No. 4-88994), and so forth.

Specific examples of such resistant strains include the following strains:
Brevibacterium flavum AJ3949 (FERM BP-2632; Japanese Patent Laid-open No. 50-113209)
Corynebacterium glutamicum AJ11628 (FERM P-5736; Japanese Patent Laid-open No. 57-065198)
Brevibacterium flavum AJ11355 (FERM P-5007; Japanese Patent Laid-open No. 56-1889)
Corynebacterium glutamicum AJ11368 (FERM P-5020; Japanese Patent Laid-open No. 56-1889)
Brevibacterium flavum AJ11217 (FERM P-4318; Japanese Patent Laid-open No. 57-2689)
Corynebacterium glutamicum AJ11218 (FERM P-4319; Japanese Patent Laid-open No. 57-2689)
Brevibacterium flavum AJ11564 (FERM BP-5472; Japanese Patent Laid-open No. 56-140895)
Brevibacterium flavum AJ11439 (FERM BP-5136; Japanese Patent Laid-open No. 56-35981)
Corynebacterium glutamicum H7684 (FERM BP-3004; Japanese Patent Laid-open No. 04-88994)
Brevibacterium lactofermentum AJ11426 (FERM P-5123; Japanese Patent Laid-open No. 56-048890)
Corynebacterium glutamicum AJ11440 (FERM P-5137; Japanese Patent Laid-open No. 56-048890)
Brevibacterium lactofermentum AJ11796 (FERM P-6402; Japanese Patent Laid-open No. 58-158192)

L-Threonine-producing Bacteria

Examples of microorganisms having L-threonine-producing ability include bacteria belonging to the family Enterobacteriaceae in which an activity of L-threonine biosynthesis system enzyme is enhanced. Examples of genes coding for L-threonine biosynthetic enzymes include the aspartokinase III gene (lysC), aspartate semialdehyde dehydrogenase gene (asd), aspartokinase I gene (thrA), homoserine kinase gene (thrB), and threonine synthase gene (thrC) encoded by the thr operon. Two or more kinds of these genes can be introduced. The genes coding for the L-threonine biosynthetic enzymes can be introduced into an Enterobacteriaceae bacterium with decreased threonine decomposition. Examples of the *Escherichia* bacterium with decreased threonine decomposition include, for example, the TDH6 strain which is deficient in threonine dehydrogenase activity (Japanese Patent Laid-open No. 2001-346578), and so forth.

The activities of the L-threonine biosynthetic enzymes are inhibited by the end product L-threonine, and therefore L-threonine biosynthetic enzymes can be modified so as to be desensitized to feedback inhibition by L-threonine when constructing L-threonine producing strains. The above-described thrA, thrB and thrC genes constitute the threonine operon which has an attenuator structure. The expression of the threonine operon is inhibited by isoleucine and threonine in the culture medium and also repressed by attenuation. This attenuation can be eliminated or reduced by removing a leader sequence or attenuator in the attenuation region (Lynn, S. P., Burton, W. S., Donohue, T. J., Gould, R. M., Gumport, R. I., and Gardner, J. F. J., Mol. Biol. 194:59-69 (1987); WO02/26993; WO2005/049808).

The native promoter present in the upstream region of the threonine operon can be replaced by a non-native promoter (WO98/04715), or the threonine operon can be constructed so that expression of the threonine biosynthetic genes is controlled by the repressor and promoter of λ-phage (European Patent No. 0593792). Furthermore, mutant *Escherichia* bacteria that are desensitized to feedback inhibition by L-threonine can be obtained by selecting strains resistant to α-amino-β-hydroxyisovaleric acid (AHV).

The copy number of the feedback-resistant threonine operon can be increased, or the expression of the modified operon can be increased by connecting it to a potent promoter. The copy number can be increased by using, in addition to amplification using a plasmid, transposon, Mu-phage, or the like so that the operon is transferred onto the chromosome.

The gene encoding aspartokinase III (lysC) can be modified so that the enzyme is desensitized to feedback inhibition by L-lysine. Such a modified lysC gene can be obtained by the method described in U.S. Pat. No. 5,932,453.

L-Threonine-producing bacteria can also be obtained by enhancing expression of genes involved in the glycolytic pathway, TCA cycle, or respiratory chain, or genes that regulate expression of these genes, or genes involved in sugar uptake, besides the L-threonine biosynthetic enzyme genes. Examples of these genes that are effective for L-threonine production include the transhydrogenase gene (pntAB, European Patent No. 733712), phosphoenolpyruvate carboxylase gene (pepC, WO95/06114), phosphoenolpyruvate synthase gene (pps, European Patent No. 877090), and pyruvate carboxylase gene derived from coryneform bacterium or *Bacillus* bacterium (WO99/18228, European Patent Laid-open No. 1092776).

L-Threonine-producing bacteria can also be obtained by enhancing expression of a gene that imparts L-threonine resistance and/or a gene that imparts L-homoserine resistance, or by imparting L-threonine resistance and/or L-homoserine resistance to the host bacterium. Examples of the genes that impart the above-mentioned resistance include the rhtA gene (Res. Microbiol. 154:123-135 (2003)), rhtB gene (European Patent Laid-open No. 0994190), rhtC gene (European Patent Laid-open No. 1013765), yfiK gene, and yeaS gene (European Patent Laid-open No. 1016710). Exemplary methods for imparting L-threonine resistance to a host bacterium include those described in European Patent Laid-open No. 0994190 or WO90/04636.

*E. coli* VKPM B-3996 (U.S. Pat. No. 5,175,107) can be exemplified as an L-threonine-producing bacterium. The strain VKPM B-3996 was deposited on Nov. 19, 1987 at the Russian National Collection of Industrial Microorganisms (VKPM), GNII Genetika (Russia, 117545 Moscow 1, Dorozhny proezd, 1) under the registration number VKPM B-3996. The VKPM B-3996 strain contains the plasmid pVIC40 (WO90/04636) which was obtained by inserting the threonine biosynthetic genes (threonine operon, thrABC) into a wide host range plasmid vector pAYC32 containing the streptomycin resistance marker (Chistorerdov, A. Y., and Tsygankov, Y. D., Plasmid, 16, 161-167 (1986)). In pVIC40, aspartokinase I-homoserine dehydrogenase I encoded by the thrA gene in the threonine operon is desensitized to feedback inhibition by threonine.

*E. coli* VKPM B-5318 (refer to European Patent No. 0593792) can also be exemplified as L-threonine-producing bacterium. The VKPM B-5318 strain was deposited in the Russian National Collection of Industrial Microorganisms (VKPM) GNII Genetika (Russia, 117545 Moscow 1, Dorozhny proezd, 1) on May 3, 1990 under a registration number of VKPM B-5318. The VKPM B-5318 strain is prototrophic with regard to L-isoleucine, and harbors a recombinant plasmid DNA constructed so that the threonine operon, i.e., threonine biosynthesis genes, deficient in the attenuator region, which is an originally contained transcription regulation region, is located downstream from the λ phage-derived temperature-sensitive C1 repressor, PR-promoter, and the gene coding for N-terminal of Cro protein, and the expression of the threonine biosynthesis genes are regulated by the repressor and the promoter derived from λ phage.

L-Glutamine-producing Bacteria

Examples of method for imparting L-glutamine-producing ability by breeding include, for example, a method of modifying a bacterium so that expression of a gene coding for an enzyme which is involved in L-glutamine biosynthesis is enhanced. Examples of the enzyme which is involved in L-glutamine biosynthesis include, for example, glutamine synthetase and glutamate dehydrogenase (Japanese Patent Laid-open No. 2002-300887).

Modifications for imparting L-glutamine-producing ability can also be attained by reducing or deleting activity of an enzyme which catalyzes a reaction branching off from the biosynthesis pathway of L-glutamine and producing another compound. For example, it is conceivable to reduce intracellular glutaminase activity (Japanese Patent Laid-open No. 2004-187684).

Examples of methods for imparting or enhancing L-glutamine-producing ability by breeding include imparting resistance to amino acid analogues and so forth. Examples further include imparting 6-diazo-5-oxo-norleucine resistance (Japanese Patent Laid-open No. 3-232497), imparting purine analogue resistance and/or methionine sulfoxide resistance (Japanese Patent Laid-open No. 61-202694), imparting α-ketomalonic acid resistance (Japanese Patent Laid-open No. 56-151495), imparting resistance to a peptide containing glutamic acid (Japanese Patent Laid-open No. 2-186994) and so forth.

Specific examples of coryneform bacteria having L-glutamine-producing ability include the following strains:
*Brevibacterium flavum* AJ11573 (FERM P-5492, see Japanese Patent Laid-open No. 56-151495)
*Brevibacterium flavum* AJ12210 (FERM P-8123, see Japanese Patent Laid-open No. 61-202694)
*Brevibacterium flavum* AJ12212 (FERM P-8123, see Japanese Patent Laid-open No. 61-202694)
*Brevibacterium flavum* AJ12418 (FERM-BP2205, see Japanese Patent Laid-open No. 2-186994)
*Brevibacterium flavum* DH18 (FERM P-11116, see Japanese Patent Laid-open No. 3-232497)
*Corynebacterium melassecola* DH344 (FERM P-11117, see Japanese Patent Laid-open No. 3-232497)
*Corynebacterium glutamicum* AJ11574 (FERM P-5493, see Japanese Patent Laid-open No. No. 56-151495)

L-Cysteine-producing Bacteria

Examples of L-cysteine-producing bacteria include, but are not limited to, strains belonging to the genus *Escherichia*, such as *E. coli* JM15 which is transformed with different cysE alleles encoding feedback-resistant serine acetyltransferases (U.S. Pat. No. 6,218,168, Russian Patent Application No. 2003121601), *E. coli* W3110 with overexpressed genes which encode proteins which promote excretion of substances toxic to cells (U.S. Pat. No. 5,972,663), *E. coli* strains with reduced cysteine desulfohydrase activity (Japanese Patent Laid-open No. 11-155571), *E. coli* W3110 with increased activity of a positive transcriptional regulator for cysteine regulon encoded by the cysB gene (WO01/27307A1), and so forth.

In the L-amino acid-producing bacteria, genes involved in sugar uptake, sugar metabolism (glycolytic pathway) and energy metabolism can be amplified in addition to the genes encoding characteristic biosynthesis enzymes.

Examples of the genes involved in sugar metabolism include the genes coding for the enzymes of the glycolytic pathway and sugar uptake genes, and include glucose-6-phosphate isomerase gene (pgi, WO01/02542), phosphoenolpyruvate synthase gene (pps, European Patent Laid-open No. 877090), phosphoglucomutase gene (pgm, WO03/04598), fructose bisphosphate aldolase gene (fbp, WO03/04664), pyruvate kinase gene (pykF, WO03/008609), transaldolase gene (talB, WO03/008611), fumarase gene (fum, WO01/02545), phosphoenolpyruvate synthase gene (pps, European Patent Laid-open No. 877090), non-PTS sucrose uptake gene (csc, European Patent Laid-open No. 149911), and sucrose-assimilating gene (scrAB operon, WO90/04636).

Examples of the genes encoding enzymes involved in energy metabolism include the transhydrogenase gene (pntAB, U.S. Pat. No. 5,830,716) and cytochrome bo-type oxidase gene (cyoB, European Patent No. 1070376).

Methods for imparting nucleic acid-producing ability to a microorganism and nucleic acid-producing bacteria will be exemplified below.

A bacterium having an ability to produce a nucleic acid can be obtained by imparting, for example, purine nucleoside auxotrophy or resistance to a drug such as purine analogue to such bacteria as described above (Japanese Patent Publication Nos. 38-23099, 54-17033, 55-45199, 57-14160, 57-41915 and 59-42895). For example, a *Bacillus* bacterium having auxotrophy or drug resistance can be obtained by treating the bacterium with mutagen which is used for usual mutagenesis treatment such as N-methyl-N'-nitro-N-nitrosoguanidine (NTG) or EMS (ethyl methanesulfonate).

Examples of *Bacillus* bacteria which produce a purine nucleoside include the following.

As a specific example of an inosine-producing strain belonging to the genus *Bacillus*, the *Bacillus subtilis* KMBS16 strain can be used. This strain is derived from the known *Bacillus subtilis* trpC2 strain (168 Marburg), wherein the purR gene encoding the purine operon repressor (purR:: spc), the purA gene encoding succinyl-AMP synthase (purA:: erm), and the deoD gene encoding purine nucleoside phosphorylase (deoD::kan) are disrupted (Japanese Patent Laid-open No. 2004-242610, U.S. Patent Published Application No. 2004166575 A1). The *Bacillus subtilis* AJ3772 strain (FERM P-2555, Japanese Patent Laid-open No. 62-014794) and so forth can also be used.

Examples of *Bacillus* bacteria having an ability to produce guanosine include the *Bacillus* bacterium which has increased IMP dehydrogenase activity (Japanese Patent Laid-open No. 3-58787), *Bacillus* bacterium which is obtained by introducing a vector which includes a gene which confers resistance to purine analogues or decoyinine into an adenine auxotrophic mutant (Japanese Patent Publication No. 4-28357), and so forth.

Examples of *Bacillus* bacteria which produce a purine nucleotide include the following.

As inosinic acid-producing *Bacillus* bacteria, inosine-producing strains of *Bacillus subtilis* which have attenuated phosphatase activity have been reported (Uchida, K. et al., Agr. Biol. Chem., 1961, 25, 804-805; Fujimoto, M., Uchida, K., Agr. Biol. Chem., 1965, 29, 249-259). Examples of guanylic acid-producing bacteria include mutants of *Bacillus* bacteria which have adenine auxotrophy, resistance to decoyinine or methionine sulfoxide and an ability to produce 5'-guanylic acid (guanosine-5'-monophosphate, henceforth referred to as "GMP") (Japanese Patent Publication No. 56-12438).

Furthermore, a xanthylic acid-producing bacterium can be constructed by methods typically used to breed coryneform bacteria, an example of which is *Corynebacterium ammoniagenes*. For example, by obtaining a PRPP amidotransferase-enhanced strain (Japanese Patent Laid-open No. 8-168383), an aliphatic amino acid-resistant strain (Japanese Patent Laid-open No. 4-262790), or a dehydroproline-resistant strain (South Korean Patent Unexamined Publication No. 2003-56490), a xanthylic acid-producing bacterium can be constructed.

Moreover, exemplary methods for breeding *Bacillus* bacteria which have an ability to produce a purine-derived substance also include enhancing activity of an enzyme which is involved in purine biosynthesis which is common to the biosynthesis of purine nucleosides and purine nucleotides, i.e., purine biosynthesis enzyme, in bacterial cells. The activity of the enzyme in the cells can be increased to a level greater than that of an unmodified strain of *Bacillus* bacterium, for example, a wild-type *Bacillus* bacterium. The phrase "activity is increased" encompasses, for example, when the number of enzyme molecules per cell is increased, and when the specific activity per enzyme molecule is increased, and so forth. For example, the activity can be increased by increasing the expression of the gene encoding the enzyme. Examples of enzymes involved in the purine biosynthesis include, for example, phosphoribosyl pyrophosphate amidotransferase, phosphoribosyl pyrophosphate synthetase (PRPP synthetase [EC: 2.7.6.1]), and so forth.

Some of the catabolites produced by metabolism of sugar sources such as glucose that flow into the pentose phosphate pathway are converted into ribose-5-phosphate via ribulose-5-phosphate. From the biosynthesized ribose-5-phosphate, phosphoribosyl pyrophosphate (PRPP) is produced, which is an indispensable precursor for purine nucleoside, histidine and tryptophan biosyntheses. Specifically, ribose-5-phosphate is converted into PRPP by phosphoribosyl pyrophosphate synthetase. Therefore, an ability to produce purine-derived substance can be imparted to a *Bacillus* bacterium by modifying it so that the activity of phosphoribosyl pyrophosphate synthetase thereof is increased.

The phrase "activity of phosphoribosyl pyrophosphate synthetase is increased" means that the activity of phosphoribosyl pyrophosphate synthetase increases as compared to that of an unmodified strain such as a wild strain or a parent strain. The activity of the phosphoribosyl pyrophosphate synthetase can be measured by, for example, the method of Switzer et al. (Methods Enzymol., 1978, 51, 3-11) or Roth et al. (Methods Enzymol., 1978, 51, 12-17). A *Bacillus* bacterium in which the activity of phosphoribosyl pyrophosphate synthetase is increased can be produced by, for example, increasing expression of a gene encoding the phosphoribosyl pyrophosphate synthetase in a *Bacillus* bacterium according to a method of using a plasmid or integrating the gene into a chromosome, which can be performed in the same manner as that of the method described in Japanese Patent Laid-open No. 2004-242610.

PRPP is an indispensable precursor for purine nucleoside. When PPRP, histidine, and tryptophan is first produced, some of these are converted into purine nucleotides and purine nucleosides by the enzymes involved in the purine biosynthesis. Examples of genes encoding such enzymes include the genes of the purine operon from *Bacillus subtilis*, specifically, genes of the purEKB-purC(orf)QLF-purMNH(J)-purD operon (Ebbole D. J. and Zalkin H., J. Biol. Chem., 1987, 262, 17, 8274-87) (at present, also called purEKBCSQLFMNHD, *Bacillus subtilis* and Its Closest Relatives, Editor in Chief: A. L. Sonenshein, ASM Press, Washington D.C., 2002, Genbank Accession No. NC_000964), and the genes of the pur regulon from *Escherichia coli* (*Escherichia* and *Salmonella*, Second Edition, Editor in Chief: F. C. Neidhardt, ASM Press, Washington D.C., 1996).

Accordingly, by enhancing expression of these genes, an ability to produce a purine-derived substance can be imparted or enhanced. In addition, genes of the purine operon are not limited to these, and genes derived from other microorganisms, animals and plants can also be used.

Examples of the method for increasing expression of the purine operon include increasing expression of genes of the purine operon in a *Bacillus* bacterium by a method of using a plasmid or integrating the genes into a chromosome or the like.

The second method for increasing expression of the purine operon includes replacing a native promoter of the purine operon with a stronger promoter, and replacing the −35 or −10 region of the native promoter with a consensus sequence.

For example, in *Bacillus subtilis* (*B. subtilis* 168 Marburg strain, ATCC 6051), the −35 sequence of the purine operon is a consensus sequence (TTGACA), but the −10 sequence is TAAGAT, which differs from the consensus sequence TATAAT (Ebbole, D. J. and H. Zalikn, J. Biol. Chem., 1987, 262, 8274-8287). Therefore, by replacing the −10 sequence (TAAGAT) with a consensus sequence, by approximating the −10 sequence (TAAGAT) close to the consensus sequence, or changing it to TATAAT, TATGAT or TAAAAT, the transcriptional activity of the purine operon can be increased. A promoter sequence can be replaced by the same method as that of the gene substitution, which is described below.

The third method for increasing expression of the purine operon includes decreasing expression of the purine operon repressor (U.S. Pat. No. 6,284,495). The phrase "expression of a purine operon repressor" includes both transcription of a purine operon gene and translation of a transcription product. Furthermore, "decreasing expression" includes decreasing the expression to be lower than that in an unmodified strain such as a wild-type Bacillus bacterium, and substantially eliminating the expression.

Expression of the purine operon repressor (purine repressor) can be decreased by, for example, treating a Bacillus bacterium with ultraviolet ray irradiation or mutagen used in a usual mutagenesis treatment such as NTG or EMS and selecting a mutant showing decreased expression of the purine repressor can be employed.

Furthermore, a Bacillus bacterium with decreased expression of the purine repressor can also be obtained by, for example, besides a mutagenesis treatment, replacing a gene encoding the purine repressor on a chromosome (purR, GenBank Accession NC_000964, coding region corresponds to the nucleotide numbers 54439 to 55293) with a corresponding gene that does not normally function (hereafter, also referred to as "disrupted-type gene") by homologous recombination utilizing a gene recombination technique (Experiments in Molecular Genetics, Cold Spring Harbor Laboratory Press (1972); Matsuyama, S, and Mizushima, S., J. Bacteriol., 1985, 162, 1196-1202).

Furthermore, an ability to produce a purine-derived substance can also be enhanced by attenuating uptake of purine-derived substances into cells. For example, the uptake of purine nucleosides by the cells can be attenuated by blocking a reaction involved in the uptake of purine nucleosides by the cells. Examples of the reaction involved in the uptake of purine nucleosides by the cells include reactions catalyzed by nucleoside permeases.

Furthermore, when a purine nucleoside is produced, activity of an enzyme which decomposes the purine nucleoside can be decreased in order to enhance the ability to produce purine nucleoside. Examples of such an enzyme include purine nucleoside phosphorylase.

Purine nucleotides biosynthesized from PRPP by enzymes involved in purine biosynthesis are dephosphorylated and thereby converted into a purine nucleoside. To efficiently cause accumulation of a purine nucleoside, an activity of purine nucleoside phosphorylases, which further degrade purine nucleosides into hypoxanthine or the like can be used. That is, an activity of a purine nucleoside phosphorylase that employs purine nucleosides such as inosine, as a substrate, can be attenuated or eliminated.

Specifically, the purine nucleoside phosphorylase activity can be decreased by disrupting the deoD and pupG genes encoding purine nucleoside phosphorylase in Bacillus bacteria. The Bacillus bacterium can be modified by disrupting one or both of the deoD and pupG genes. As the deoD and pupG genes, for example, those genes derived from Bacillus bacteria (deoD; Genbank Accession No. NC_000964, coding region: 2134672-2135370), pupG; Genbank Accession No. NC_000964, coding region: 2445610-2446422) can be used.

The ability to produce a purine-derived substance can also enhanced by decreasing the activity of succinyl-AMP synthase. Examples of the gene encoding succinyl-AMP synthase include the purA gene. Examples of the purA gene include, for example, those having the nucleotide sequence registered as GenBank Accession No. NC_000964 (coding region corresponds to the nucleotide numbers 4153460 to 4155749 of the complementary strand).

The ability to produce a purine-derived substance can also be enhanced by decreasing an activity of inosine monophosphate (IMP) dehydrogenase. Examples of the gene encoding IMP dehydrogenase include the guaB gene. Examples of the guaB gene include, for example, those having the nucleotide sequence registered as GenBank Accession No. NC_000964 (coding region corresponds to the nucleotide numbers 15913 to 17376).

Moreover, as a method for enhancing an ability to produce purine-derived substance, amplification of a gene encoding a protein having an activity of excreting a purine-derived substance can be contemplated. An example of a bacterium in which such a gene has been amplified is a Bacillus bacterium in which the rhtA gene is amplified (Japanese Patent Laid-open No. 2003-219876).

When the aforementioned L-amino acid-producing bacteria are bred by gene recombination, the genes to be used are not limited to genes having the genetic information mentioned above or genes having known sequences, but also include genes having conservative mutations, such as homologues or artificially modified genes, can also be used so long as the functions of the encoded proteins are not degraded. That is, they can be genes encoding a known amino acid sequence containing one or more substitutions, deletions, insertions, additions or the like of one or several amino acid residues at one or several positions.

Although the number of the "one or several" amino acid residues referred to herein can differ depending on the position in the three-dimensional structure or the types of amino acid residues of the protein, specifically, it can be 1 to 20, 1 to 10 in another example, 1 to 5 in another example. The conservative mutation is a mutation wherein substitution takes place mutually among Phe, Trp, and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Typical examples of a conservative mutation are conservative substitutions, and substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitutions, deletions, insertions, additions, inversions or the like can be a result of a naturally-occurring mutation or a variation due to an individual difference or difference of species of a microorganism from which the genes are derived. Such genes can be obtained by, for example, modifying a known nucleotide sequence of a gene by site-specific mutagenesis so that the amino acid residues at the specific sites of the encoded protein include substitutions, deletions, insertions, or additions of amino acid residues.

Furthermore, such genes having conservative mutations as mentioned above can encode a protein having a homology of 80% or more, or in another example, 90% or more, or in another example 95% or more, or in another example 97% or more, to the entire encoded amino acid sequence and having a function equivalent to that of the wild-type protein.

Moreover, codons in the gene sequences can be replaced with other codons which are easily used in the host into which the genes are introduced.

The genes having conservative mutation(s) can be obtained by methods usually used in mutagenesis treatments such as treatments with mutagenesis agents.

Furthermore, the genes can be a DNA which can hybridize with a complementary sequence of a known gene sequence or a probe which can be prepared from the complementary sequence under stringent conditions and encodes a protein having a function equivalent to that of the known gene product. The "stringent conditions" referred to here are conditions under which a so-called specific hybrid is formed, and a non-specific hybrid is not formed. Examples of the stringent conditions include those under which highly homologous DNAs hybridize to each other, for example, DNAs not less than 80% homologous, or in another example not less than 90% homologous, or in another example not less than 95% homologous, or in another example not less than 97% homologous, hybridize to each other, and DNAs less homologous than the above do not hybridize to each other, or conditions of washing once, or 2 or 3 times, at a salt concentration and temperature corresponding to washing of typical Southern hybridization, i.e., 1×SSC, 0.1% SDS at 60° C., or in another example, 0.1×SSC, 0.1% SDS at 60° C., or in another example 0.1×SSC, 0.1% SDS at 68° C.

As the probe, a part of the sequence which is complementary to the gene can also be used. Such a probe can be prepared by PCR using oligonucleotides prepared on the basis of a known gene sequence as primers and a DNA fragment containing the nucleotide sequence as a template. For example, when a DNA fragment having a length of about 300 by is used as the probe, the washing conditions of hybridization can be 50° C., 2×SSC and 0.1% SDS.

EXAMPLES

Hereinafter, the present invention will be specifically explained with reference to following non-limiting examples.

Example 1

Production of L-Tryptophan

As an L-tryptophan-producing bacterium, *E. coli* No. 202 (refer to WO2005/103275) was used. This strain is a strain obtained by inserting the phosphoglycerate dehydrogenase gene (serA, derived from the plasmid pGH5, refer to WO94/08031) and the trp operon (derived from the plasmid pGX100) containing a desensitized type trpE gene (derived from *E. coli* MTR#2 strain, refer to U.S. Pat. No. 4,371,614) into the chromosome of an L-tryptophan-producing bacterium, the SV164 strain (refer to WO94/08031).

A glycerol stock of *E. coli* No. 202 was inoculated onto LB-agarose plate medium (1% of tryptone, 0.5% of yeast extract, 0.5% of sodium chloride and 1.5% of agarose) in an amount corresponding to one loop, and stationary culture was performed at 30° C. for 24 hours.

10 µl of the aforementioned culture medium was inoculated into 50 ml of LB medium (1% of tryptone, 0.5% of yeast extract and 0.5% of sodium chloride) contained in a 500-ml Sakaguchi flask, and pre-culture was performed at 30° C. for 8 hours with shaking (114 rpm).

0.9 ml of the aforementioned pre-culture medium was inoculated into 300 ml of a seed culture medium having the following composition. Culture was performed at 30° C. for about 14 hours using a small fermentation tank having a total volume of 1 L with a power density of a stirring impeller of 4.4 kW/m$^3$ and aeration of compressed air sterilized with a sterilization filter at 1 vvm. During the culture, temperature was maintained at 30° C., and pH was maintained at 6.5 with ammonia gas.

Composition of seed culture medium:

| Glucose | 10 g/L |
|---|---|
| KH$_2$PO$_4$ | 1 g/L |
| (NH$_4$)$_2$SO$_4$ | 2.5 g/L |
| MgSO$_4$•7H$_2$O | 0.5 g/L |
| FeSO$_4$•7H$_2$O | 10 mg/L |
| MnSO$_4$•4H$_2$O | 10 mg/L |
| Soybean hydrolysate | 0.4 g/L |
| L-Methionine | 50 mg/L |
| L-Phenylalanine | 125 mg/L |
| L-Tyrosine | 125 mg/L |
| Vitamin B1 | 5 mg/L |
| Pyridoxine | 30 mg/L |

A main culture medium having the following composition was prepared in a volume of 300 ml, and 30 ml of the seed culture medium was inoculated. The main culture was performed at 31° C. using a small fermentation tank having a total volume of 1 L with stirring at 4.4 kW/m$^3$ and aeration of compressed air sterilized with a sterilization filter at 1 vvm. During the culture, temperature was maintained at 31° C., and pH was maintained at 6.7 with ammonia gas. During the culture, a 700 g/L glucose solution was appropriately fed to adjust the saccharide concentration in the small fermentation tank to be 5 to 20 g/L. After 23 hours of the culture, 10 g of L-tryptophan crystals (33 g/L) were added, and the culture was performed with four different levels of power density of the stirring impeller, 2.4 kW/m$^3$, 5.5 kW/m$^3$, 15.5 kW/m$^3$ and 19.9 kW/m$^3$.

Composition of main culture medium:

| Glucose | 15 g/L |
|---|---|
| KH$_2$PO$_4$ | 1 g/L |
| (NH$_4$)$_2$SO$_4$ | 1 g/L |
| Soybean hydrolysate | 0.75 g/L |
| NaCl | 0.5 g/L |
| MgSO$_4$•7H$_2$O | 0.3 g/L |
| CaCl$_2$•2H$_2$O | 14.7 mg/L |
| FeSO$_4$•7H$_2$O | 10 mg/L |
| MnSO$_4$•4H$_2$O | 7.5 mg/L |
| L-Methionine | 0.3 g/L |
| L-Phenylalanine | 1 g/L |
| Vitamin B1 | 5 mg/L |
| Pyridoxine | 36.5 mg/L |
| NH$_4$Cl | 3.13 g/L |
| KOH | 1 g/L |

Figure 2:
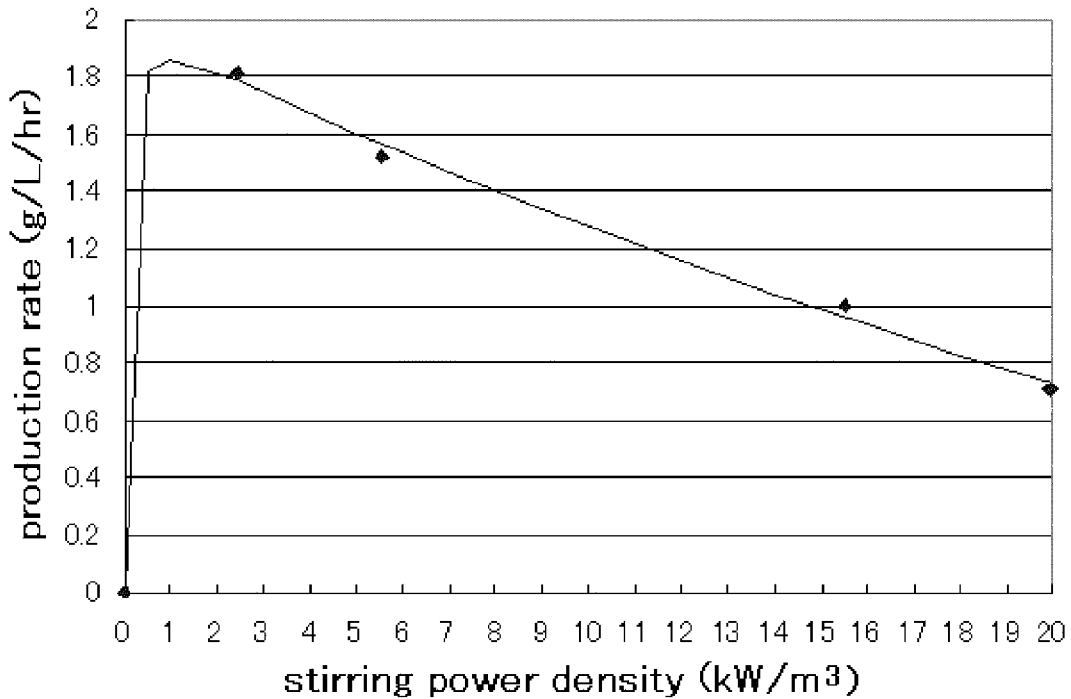
FIG. 2 shows the relation of the power density of the stirring impeller and the production rate of L-tryptophan.

After 46 hours of the culture, L-tryptophan concentration in the medium was measured, and production rate was calculated. The results are shown in FIG. 2. Although the culture was not performed at a power density of 0, the plotting was performed also for power density of 0 in FIG. 2 in order to create an approximated curve. The production rate was expressed as relative values based on the production rate obtained with a stirring power density of 15.5 kW/m³, which was taken as 1.

Reference Example 1

Construction of L-Glutamic Acid-producing Bacterium

The primer 1 (SEQ ID NO: 1) and the primer 2 (SEQ ID NO: 2) for amplifying a part of the plasmid RSFCPG (European Patent Laid-open No. 1233068) which contains the gltA, ppc and gdhA genes derived from *Escherichia coli* were designed to amplify the part other than the gltA ORF. Using these primers and RSFCPG as a template, PCR was performed to obtain a fragment of about 14.9 kb. PCR was also performed using the primer 3 (SEQ ID NO: 3), the primer 4 (SEQ ID NO: 4) and the chromosomal DNA of the *E. coli* W3110 strain as a template to obtain a fragment of about 1.2 kb containing the methylcitrate synthase gene (prpC). Both the PCR products were treated with BglII and KpnI, ligated, and then used to transform the *E. coli* JM109 strain. All the appeared colonies were collected, and plasmids were extracted from the cells as a mixture. The *E. coli* ME8330 strain as a citrate synthase (CS) deficient strain was transformed with the plasmid mixture, and the cell suspension was applied onto the M9 minimal medium (medium containing 5 g of glucose, 2 mM magnesium sulfate, 3 g of monopotassium phosphate, 0.5 g of sodium chloride, 1 g of ammonium chloride and 6 g of disodium phosphate in 1 L of pure water) containing 50 mg/L of uracil and 5 mg/L of thiamine HCl. From the emerged strains, a plasmid was extracted and designated RSFPPG. This L-glutamic acid production plasmid RSFPPG was introduced into the *Pantoea ananatis* SC17sucA strain to construct an L-glutamic acid-producing strain, SC17sucA/RSFPPG (this strain is referred to as "NA1 strain").

The aforementioned SC17sucA strain is obtained by obtaining a low phlegm production mutant strain (SC17) from the AJ13355 strain, which was isolated from the nature as a strain that could proliferate in a medium containing L-glutamic acid and a carbon source at low pH, and disrupting the sucA gene of the mutant strain (U.S. Pat. No. 6,596,517). The SC17sucA strain was assigned a private number of AJ417, deposited at the National Institute of Bioscience and Human-Technology, Agency of Industrial Science and Technology, Ministry of Economy, Trade and Industry (currently National Institute of Advanced Industrial Science and Technology, International Patent Organism Depositary, Tsukuba Central 6, 1-1, Higashi 1-Chome, Tsukuba-shi, Ibaraki-ken, Japan, postal code: 305-8566) on Feb. 26, 2004, and assigned an accession number of FERM BP-08646.

Example 2

Production of L-Glutamic Acid

A glycerol stock of the glutamic acid-producing bacterium, *Pantoea ananatis* NA1, was inoculated onto an LBGM9-agarose plate medium (1% of tryptone, 0.5% of yeast extract, 1.05% of sodium chloride, 0.5% of glucose, 0.05% of magnesium sulfate 7 hydrate, 1.72% of disodium hydrogenphosphate 12 hydrate, 0.3% of potassium dihydrogenphosphate, 0.1% of ammonium chloride, 2% of agarose, 25 mg/L of tetracycline hydrochloride) in an amount corresponding to one loop, and stationary culture was performed at 34° C. for 24 hours.

The above pre-cultured bacterial cells corresponding to one culture dish were inoculated into 300 ml of a medium having the following composition. Culture was performed by using a small fermentation tank having a total volume of 1 L with a power density of a stirring impeller of 3.3 kW/m³ and aeration of compressed air sterilized with a sterilization filter at 1 vvm. During the culture, temperature was maintained at 34° C., and pH was maintained at 4.7 with ammonia gas. After 20 hours of the culture, a 700 g/L sucrose solution was appropriately fed to adjust the saccharide concentration in the small fermentation tank to be 5 to 20 g/L. After 20 hours of the culture, 20 g of α-crystals of L-glutamic acid were added, and the culture was performed with three different levels of power density of the stirring impeller, 2.4 kW/m³, 15.5 kW/m³ and 19.9 kW/m³.

Medium composition:

| | |
|---|---|
| Sucrose | 100 g/L |
| $MgSO_4 \cdot 7H_2O$ | 0.4 g/L |
| $(NH_4)_2SO_4$ | 5 g/L |
| $KH_2PO_4$ | 6 g/L |
| Yeast extract | 6 g/L |
| NaCl | 1.5 g/L |
| $FeSO_4 \cdot 7H_2O$ | 20 mg/L |
| $MnSO_4 \cdot 4H_2O$ | 20 mg/L |
| L-Lysine hydrochloride | 0.6 g/L |
| DL-Methionine | 0.6 g/L |
| Diaminopimelic acid | 0.6 g/L |
| $CaCl_2 \cdot 2H_2O$ | 2.64 mg/L |
| $ZnSO_4 \cdot 7H_2O$ | 0.72 mg/L |
| $CuSO_4 \cdot 5H_2O$ | 0.64 mg/L |
| $CoCl_2 \cdot 6H_2O$ | 0.72 mg/L |
| $H_3BO_3$ | 0.4 mg/L |
| $Na_2MoO_4 \cdot 2H_2O$ | 1.2 mg/L |
| Tetracycline hydrochloride | 25 mg/L |

Figure 3:
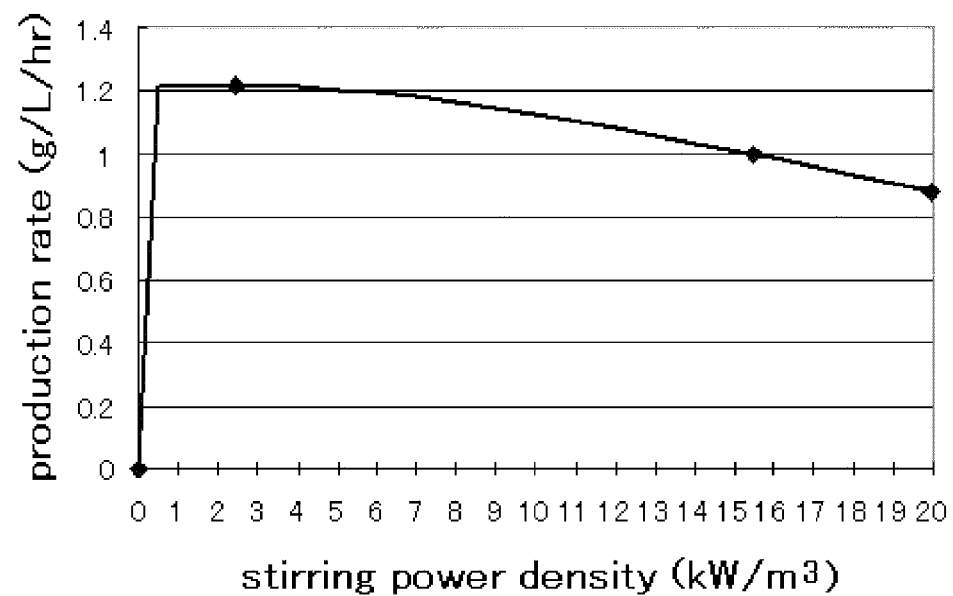
FIG. 3 shows the relation of power density of the stirring impeller and the production rate of L-glutamic acid.

After 49 hours of the culture, L-glutamic acid concentration in the medium was measured, and production rate was calculated. The results are shown in FIG. 3. The production rate was expressed as relative values based on the production rate obtained with a stirring power density of 15.5 kW/m₃, which was taken as 1.

Example 3

Production of L-Threonine

As an L-threonine-producing bacterium, *E. coli* VKPM B-5318 (European Patent Laid-open No. 0593792) was used.

A glycerol stock of *E. coli* VKPM B-5318 was inoculated onto LB-agarose plate medium (1% of tryptone, 0.5% of yeast extract, 0.5% of sodium chloride, 1.5% of agarose, 100 mg/L of tetracycline sulfate) in an amount corresponding to one loop, and stationary culture was performed at 37° C. for 24 hours.

The aforementioned culture medium was inoculated into an amount corresponding to 1/10 of the plate to 50 ml of LB medium (1% of tryptone, 0.5% of yeast extract, 0.5% of sodium chloride, 25 mg/L of kanamycin sulfate and 20 mg/L of streptomycin sulfate) contained in a 500-ml Sakaguchi flask, and pre-culture was performed at 40° C. for 4 hours with shaking (114 rpm).

A main culture medium having the following composition was prepared in a volume of 300 ml, and 30 ml of the seed culture medium was inoculated. The main culture was performed at 40° C. by using a small fermentation tank having a total volume of 1 L with stirring at 5.5 kW/m³ and aeration of compressed air sterilized with a sterilization filter at 1 vvm.

During the culture, the temperature was maintained at 40° C., and pH was maintained at 7.0 with ammonia gas. During the culture, a 700 g/L sucrose solution was appropriately fed to adjust the saccharide concentration in the small fermentation tank to be 5 to 20 g/L. After 21 hours of the culture, 24 g of L-threonine crystals (70 g/L) were added, and the culture was performed with three different levels of power density of the stirring impeller, 2.4 kW/m$^3$, 5.5 kW/m$^3$ and 13.5 kW/m$^3$.

Composition of main culture medium:

| | |
|---|---|
| Sucrose | 40 g/L |
| MgSO$_4$•7H$_2$O | 0.36 g/L |
| (NH$_4$)$_2$SO$_4$ | 4.5 g/L |
| FeSO$_4$•7H$_2$O | 18 mg/L |
| MnSO$_4$•4H$_2$O | 18 mg/L |
| K$_2$HPO$_4$ | 1.5 g/L |
| NaCl | 0.6 g/L |
| Yeast Extract | 1.8 g/L |
| Kanamycin sulfate | 25 mg/L |
| Streptomycin sulfate | 25 mg/L |

Figure 4:
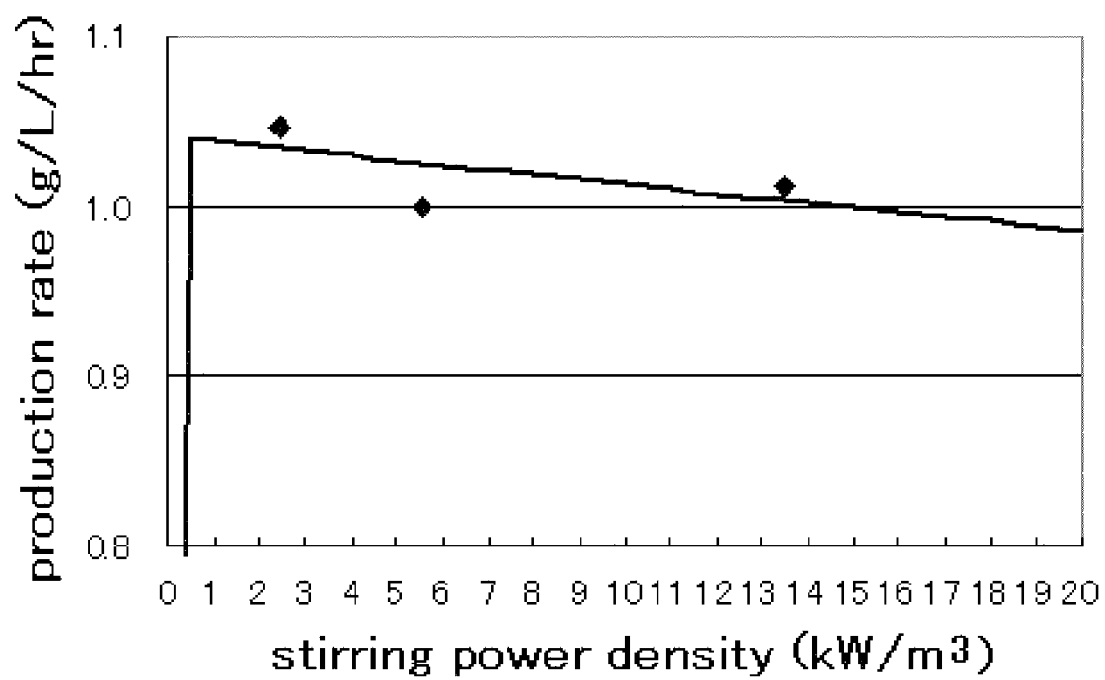
FIG. 4 shows the relation of power density of the stirring impeller and the production rate of L-threonine.

After 45 hours of the culture, L-threonine concentration in the medium was measured, and production rate was calculated. The results are shown in FIG. 4. The production rate was represented with relative values based on the production rate obtained with a stirring power density of 5.5 kW/m$^3$, which was taken as 1.

Example 4

Production of L-Phenylalanine

As an L-phenylalanine-producing bacterium, *E. coli* AJ12741 strain (Japanese Patent No. 3225597, henceforth also referred to as "R/GAL strain") is used. This strain is a strain obtained by introducing the aroG4 gene coding for 3-deoxy-D-arabinoheptulosonate-7-phosphate synthase desensitized to feedback inhibition, pheA gene coding for chorismate mutase/prephenate dehydratase and aroL gene coding for shikimate kinase into the *Escherichia coli* K-12 W3110 strain deficient in the tyrR and tyrA genes. This strain was deposited at the independent administrative agency, National Institute of Advanced Industrial Science and Technology, International Patent Organism Depositary (Address: Tsukuba Central 6, 1-1, Higashi 1-Chome, Tsukuba-shi, Ibaraki-ken, 305-8566, Japan) on Jun. 11, 1992 and assigned an accession number of FERM P-13000. Then, the deposition was converted into an international deposit under the provisions of the Budapest Treaty on Sep. 14, 1994, and an accession number of FERM BP-4796 was assigned.

A glycerol stock of the AJ12741 strain is inoculated onto LBG-agarose plate medium (1% of tryptone, 0.5% of yeast extract, 0.5% of sodium chloride and 1.5% of agarose) in an amount corresponding to one loop, and stationary culture is performed at 35° C. for 24 hours.

The aforementioned cultured bacterial cells corresponding to one culture dish are inoculated to 300 mL of a medium having the following composition. Culture was performed for about 16 hours by using a small fermentation tank having a total volume of 1 L with stirring at a power density of a stirring impeller of 3.3 kW/m$^3$ and aeration of compressed air sterilized with a sterilization filter at 1 vvm. During the culture, temperature is maintained at 35° C., and pH is maintained at 6.5 with ammonia gas.

Composition of seed culture medium:

| | |
|---|---|
| Glucose | 40 g/L |
| MgSO$_4$ | 1 g/L |
| (NH$_4$)$_2$SO$_4$ | 16 g/L |
| KH$_2$PO$_4$ | 1 g/L |
| Yeast extract | 2 g/L |
| FeSO$_4$•7H$_2$O | 10 mg/L |
| MnSO$_4$•4H$_2$O | 8 mg/L |
| L-Tyrosine | 1 g/L |
| Sodium ampicillin | 100 mg/L |

A main culture medium having the following composition is prepared in a volume of 300 ml, and 30 ml of the seed culture medium is inoculated. The main culture is performed at 35° C. by using a small fermentation tank having a total volume of 1 L with stirring at a power density of the stirring impeller of 3.3 kW/m$^3$ and aeration of compressed air sterilized with a sterilization filter at 1 vvm. During the culture, temperature is maintained at 35° C., and pH is maintained at 6.5 with ammonia gas. During the culture, a 500 g/L glucose solution is appropriately fed to adjust the saccharide concentration in the small fermentation tank to be 5 to 20 g/L. Furthermore, after 24 hours of the culture, 20 g of L-phenylalanine crystals are added, and the culture is performed with four different levels of power density of the stirring impeller, 5.5 kW/m$^3$, 15.5 kW/m$^3$ and 19.9 kW/m$^3$, and a power density controlled to be 2.4 kW/m$^3$ or lower.

Composition of main culture medium:

| | |
|---|---|
| Glucose | 40 g/L |
| MgSO$_4$ | 1 g/L |
| (NH$_4$)$_2$SO$_4$ | 16 g/L |
| KH$_2$PO$_4$ | 2 g/L |
| Yeast extract | 8 g/L |
| FeSO$_4$•7H$_2$O | 10 mg/L |
| MnSO$_4$•4H$_2$O | 8 mg/L |
| L-Tyrosine | 1.4 g/L |
| Sodium ampicillin | 100 mg/L |

Example 5

Production of Inosine and/or Guanosine

A glycerol stock of the *Bacillus amyloliquefaciens* AJ1991 strain (VKPM B-8994, refer to U.S. Pat. No. 3,575,809), which produces inosine and guanosine, is inoculated onto LBG-agarose plate medium (1% of tryptone, 0.5% of yeast extract, 1% of sodium chloride and 1.5% of agarose) in an amount corresponding to one loop, and stationary culture is performed at 34° C. for 24 hours. The AJ1991 strain was also designated G1136A strain, deposited on Mar. 10, 2005 at the Russian National Collection of Industrial Microorganisms (VKPM), GNII Genetika (Russia, 117545 Moscow, 1st Dorozhny proezd, 1), and assigned an accession number VKPM B-8994. The deposition was then converted to an international deposit on Oct. 13, 2006.

The pre-cultured cells of the aforementioned bacterium are inoculated in an amount corresponding to one platinum loop into 50 ml of a medium having the following composition contained in a 500-ml Sakaguchi flask, and pre-culture is performed at 34° C. for 16 hours with shaking (115 rpm).

Composition of seed culture medium:

| Glucose | 30 g/L |
|---|---|
| NH$_4$Cl | 3 g/L |
| KH$_2$PO$_4$ | 0.5 g/L |
| MgSO$_4$•7H$_2$O | 0.4 g/L |
| FeSO$_4$•7H$_2$O | 10 mg/L |
| MnSO$_4$•4H$_2$O | 10 mg/L |
| Soybean hydrolysate | 1.2 g/L |
| Yeast extract | 0.5 g/L |
| ribonucleic acid | 5 g/L |

A main culture medium having the following composition is prepared in a volume of 300 ml, and 15 ml of the seed culture medium is inoculated. The main culture is performed at 34° C. by using a small fermentation tank having a total volume of 1 L with stirring at a power density of the stirring impeller of 3.3 kW/m$^3$ and aeration of compressed air sterilized with a sterilization filter at 1 vvm. During the culture, temperature is maintained at 34° C., and pH is maintained at 6.5 with ammonia gas. During the culture, a 500 g/L glucose solution is appropriately fed to adjust the saccharide concentration in the small fermentation tank to be 5 to 20 g/L. After 24 hours of the culture, 0.8 g of guanosine crystals are added, and the culture is performed under four kinds of conditions of the power density of the stirring impeller, 5.5 kW/m$^3$, 15.5 kW/m$^3$ and 19.9 kW/m$^3$, and a power density controlled to be 2.4 kW/m$^3$ or lower.

Composition of main culture medium:

| Glucose | 200 g/L |
|---|---|
| NH$_4$Cl | 2.5 g/L |
| KH$_2$PO$_4$ | 1.3 g/L |
| MgSO$_4$•7H$_2$O | 1.5 g/L |
| FeSO$_4$•7H$_2$O | 10 mg/L |
| MnSO$_4$•4H$_2$O | 10 mg/L |
| Soybean hydrolysate | 1.3 g/L |
| Ribonucleic acid | 1.24 g/L |
| KCl | 15 g/L |
| DL-Methionine | 50 mg/L |

Industrial Applicability

According to the present invention, in a method for producing an L-amino acid or a nucleic acid by fermentation using a microorganism having an L-amino acid or nucleic acid-producing ability, productivity of the L-amino acid or nucleic acid is improved. The improvement of productivity of L-amino acid or nucleic acid includes improvement in yield based on saccharide and/or improvement in production rate.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing an L-amino acid or a nucleic acid comprising:
   A) culturing a microorganism having an ability to produce the L-amino acid or nucleic acid in a liquid medium in a fermentation tank containing a stirring impeller, and optionally adding seed crystals to the medium as required,
   B) allowing crystals of the L-amino acid or nucleic acid to accumulate in the medium, and
   C) collecting crystals of the L-amino acid or nucleic acid from the medium, wherein the power density of the stirring impeller is controlled to be 2.4 kW/m$^3$ or lower after either precipitation of the crystals or the addition of the seed crystals.

2. The method according to claim 1, wherein the power density of the stirring impeller is controlled to be 0.5 kW/m$^3$ or higher after either precipitation of the crystals or addition of the seed crystals.

3. The method according to claim 1, wherein the power density of the stirring impeller is controlled to be 3.0 kW/m$^3$ or higher before either precipitation of the crystals or addition of the seed crystals.

4. The method according to claim 1, wherein the microorganism belongs to the family Enterobacteriaceae.

5. The method according to claim 1, wherein the microorganism is a coryneform bacterium or a *Bacillus* bacterium.

6. The method according to claim 1, wherein the L-amino acid is selected from the group consisting of L-tryptophan, L-phenylalanine, L-tyrosine, L-isoleucine, L-valine, L-leucine, L-glutamic acid, L-glutamine, L-threonine, L-cysteine, L-cystine, derivatives thereof, and combinations thereof.

7. The method according to claim 1, wherein the nucleic acid is selected from the group consisting of inosine, adenosine, guanosine, xanthosine, inosinic acid, adenylic acid, guanylic acid, xanthylic acid, derivatives thereof, and combinations thereof.

8. The method according to claim 4, wherein the microorganism is *Escherichia coli* or *Pantoea ananatis*.

9. The method according to claim 5, wherein the microorganism is *Corynebacterium glutamicum* or *Bacillus amyloliquefaciens*.

* * * * *